US005525623A

United States Patent [19]

Spear et al.

[11] Patent Number: 5,525,623

[45] Date of Patent: Jun. 11, 1996

[54] COMPOSITIONS AND METHODS FOR THE TREATMENT OF IMMUNOMEDIATED INFLAMMATORY DISORDERS

[75] Inventors: Kerry Spear, Oakland; Charles Johnson, Berkeley; Heinz W. Gschwend, Bodega Bay, all of Calif.

[73] Assignee: Arris Pharmaceutical Corporation, South San Francisco, Calif.

[21] Appl. No.: 212,169

[22] Filed: Mar. 11, 1994

Related U.S. Application Data

[63] Continuation-in-part of Ser. No. 31,187, Mar. 12, 1993, abandoned.

[51] Int. Cl.$^6$ .......................... A61K 31/40; C07D 207/00

[52] U.S. Cl. .......................... 514/423; 548/533; 548/537

[58] Field of Search .......................... 548/533, 537; 514/423

[56] References Cited

U.S. PATENT DOCUMENTS 4,201,863 5/1980 Okamoto et al. .......................... 546/166
4,456,595 6/1984 Weller, III et al. .......................... 424/177

OTHER PUBLICATIONS

Katunuma, et al., 1990, "Recent Advances in Research on Tryptases and Endogenous Tryptase Inhibitors," Schwartz (ed): Neutral Proteases of Mast Cells, *Monogr. Allergy*, Basel, Karger, 27:pp. 51–66.

Lavens et al., (1992), Program and Abstracts, X Int'l. Congress of Eye Research, *The Int'l. Soc. for Eye Research*, 91:(1) (Part 2), Abstract No. 760, p. 331, "Release of Tryptase from Human Lung Mast Cells(HLMC)".

Walls et al., (1993), *J. Allergy Clin Immunol.*, Abstract No. 462, p. 256, "Mast Cell Proteases as Mediators of Vascular Leakage and Cell Accumulation".

Lilly et al., (1992), *Am. Lung Assoc. Meeting*, "Ovalbumin Induced Pulmonary Inflammation Inhibits VIP Pulmonary Relaxation in Superfused Guinea Pig Lungs," p. A36.

Lilly et al., (1993), *J. Clin. Invest.*, 91:pp. 235–243, "Peptidase Modulation of Vasoactive Intestinal Peptide Pulmonary Relaxation in Tracheal Superfused Guinea Pig Lungs".

Tam et al., (1990), *Am. J. Respir. Cell Mol. Biol.*, 3:pp. 27–32, "Degradation of Airway Neuropeptides by Human Lung Tryptase".

Tam et al., (1990), *Am. J. Respir. Cell Mol. Biol.*, 2:pp. 449–452, "Protease Inhibitors Potentiate Smooth Muscle Relaxation Induced by Vasoactive Intestinal Peptide in Isolated Human Bronchi".

Issekutz et al., (1990), *Int. J. Immunopharmac.*, 12(1), ;pp. 1–9, "The Effect of FUT–175 (Nafamstat Mesilate) on $C3_aC4_a$ and $C5_a$ Generation In Vitro and Inflammatory Reactions In Vivo".

Barnes, (1991), *TIBS*, 16:pp. 365–369, "Biochemistry of Asthma".

Spragg et al., (1988), *Peptides*, 9:pp. 203–206, "The Inhibition of Glandular Kallikrein by Peptide Analog Antagonists of Bradykinin".

Slapke et al., (1986), *Eur. J. Respir Dis.*, 68:pp. 29–34, "Protease Inhibitor Prevents Bronchoconstriction in Man".

Spragg et al., (1989, *Adv. Exp. Med. Biol., 247B:pp. 277–281, "Inhibition of Human and Rat Tissue Kallikreins by Peptide Analog"*.

Abraham et al., (1991), *Am. Rev. Respir. Dis.*, 143:pp. 787–796, "A Bradykinin Antagonist Modifies Allergen–Induced Mediator Release and Late Bronchial Responses in Sheep".

Soler et al., (1990), *Pulmonary Pharmacology*, 3:pp. 9–15, "A Bradykinin–Antagonist Blocks Antigen–Induced Airway Hyperresponsiveness and Inflammation in Sheep".

Caughey et al., (1988), *J. Pharm. and Experimental Therapeutics*, 244(1):133–137, "Substance P and Vasoactive Intestinal Peptide Degradation by Mast Cell Tryptase and Chymase".

Caughey, (1991), *Am. J. Respir. Cell Mol. Biol.*, 4:pp. 387–394, "The Structure and Airway Biology of Mast Cell Proteinases".

Tidwell, (1978), *J. Medicinal Chem.*, 21(7):pp. 613–623, "Diary–lamidine Derivatives with One or Both of the Aryl Moieties Consisting of an Indole or Indole–Like Ring. Inhibitors of Arginine–Specific Esteroproteases".

Barnes, (1991), British Medicine Bulletin 48(1):pp. 231–247, "New Therapeutic Approaches".

Sekizawa et al., (1989) *J. Clin Invest.*, 83:pp. 175–179, "Mast Cell Tryptase Causes Airway Smooth Muscle Hyper–responsiveness in Dogs".

Franconi, et al., (1989), *J. Pharm. and Experim. Therapeutics*, 248(3) ;pp. 947–951, "Mast Cell Tryptase and Chymase Reverse Airway Smooth Muscle Relaxation Induces by Vasoactive Intestinal Peptide in the Ferret".

Stürzebecher et al., (1992), *Biol. chem. Hoppa Seyer* 373: pp. 1025–1030, "Inhibition of Human Mast Cell Tryptase by Benzamidine Derivatives".

Misawa et al., (1987), *Japan J. Pharmocol.*, 43:pp. 53–60, "The Effect of Trans–4–Gaunidinomethylcyclohexanecarboxylic Acid p–tert–Butylphenyl Ester Hydrochloride (NCO–650) on Ascaris Suum Antigen–Induced Bronchoconstriction in Dogs".

Smith et al., (1984), *J. Biol. Chem.*, 259(17):pp. 11046–11051, "Human Lung Tryptase".

Caughey, et al., (1987), *Archives Biochem. and Biophysics.*, 258(2):pp. 555–563, "Dog Mastocytoma Tryptase: Affinity Purification, Characterization, and Amino–Terminal Sequence".

(List continued on next page.)

*Primary Examiner*—Johann Richter
*Attorney, Agent, or Firm*—Townsend & Townsend & Crew

[57] ABSTRACT

Compositions and methods for the prevention and treatment of immunomediated inflammatory disorders, especially for those disorders associated with the respiratory tract, are provided. More particularly, a tryptase inhibitor, typically a hydroxyaroyl or hydroxyheteroaroyl substituted dipeptide, is administered. Also provided by this invention are pharmaceutical compositions, typically aerosol or topical, as well as aerosol devices for administering these compositions intranasally.

118 Claims, 1 Drawing Sheet

OTHER PUBLICATIONS

Oda et al., (1990), 'Japan J. Pharmacol., 52:pp. 23-34, "Pharmacological Studies on 6-Amidino-2-Naphthy . . . and Anticomplement Activity In Vivo".

Matsuoka et al., (1989), *Japan J. Pharmacol.,* 51:pp. 455–463, "Inhibitory Effects of ONO-3307 on Various Proteases and Tissue Thromboplastin In Vitro and on Experimental Thrombosis In Vivo".

Ueda et al., (1990), *Biochem. J.,* 265:pp. 539-545, "The Synthesis of Arginylfluoroalkanes, Their Inhibition of Trypsin and Blood-Coagulation Serine Proteinases and Their Anticoagulant Activity".

Harvima et al., (1988), *Biochimica et Biophysica Acta.,* 957:71–80, "Human Skin Tryptase: Purification, Partial Characterization and Comparison with Human Lung Tryptase".

Alter et al., 1990), *Archives Biochem. and Biophysics.,* 276(1):pp. 26–31, "Interactions of Human Mast Cell Trypotase with Biological Protease Inhibitors".

Caughey et al., (1993), "Bis (5-Amidino-2-Benzimidazolyl) Methane and Related Amidines Are Potent, Reversible Inhibitors of Mast Cell Tryptases," *J. Pharmacol. and Exper. Therapeutics,* 264(2): 676. Galley proof submitted.

Walls et al., (1992), *Biochem. Pharmacol.,* 43(6):pp. 1243–1248, Printed in Great Britain, "Human Mast Cell Tryptase Attenuates the Vasodilator Activity of Calcitonin Gene-Related Peptide".

Muramatsu et al., (1982), *Hoppe-Seyler's Z. Physiol. Chem.,* Bd. 363, S. pp. 203–211, "Inhibitory Effects of Aryl . . . and Their Antiallergic Effects".

Vanderslice et al., (1990), *Proc. Natl. Acad. Sci. USA,* 87:pp. 3811-3815, "Human Mast Cell Tryptase: Multiple cDNAs and Genes Reveal a Multigene Serine Protease Family".

Miller et al., (1990), *J. Clin. Invest.,* 864-870, "Cloning and Characterization of a Second Complementary DNA for Human Tryptase".

Miller et al., (1989), *J. Clin. Invest.,* 84:pp. 1188-1195, "Cloning and Characterization of Complementary DNA for Human Tryptase".

Vanderslice et al., (1989), *Am. Chem. Soc.,* 28:4148–4155, "Molecular Cloning of Dog Mast Cell Tryptase and a Related Protease: Structural Evidence of a Unique Mode of Serine Protease Activation".

Schwartz et al., (1987), *N. Engl. J. Med.,* 316(26):pp. 1622-1626, "Tryptase Levels as an Indicator of Mast-Cell Activation in Systematic Anaphylaxis and Mastocytosis".

Castells et al., (1988), *J. Allerg. Clin. Immunol.,* 82:pp. 348-355, "Tryptase Levels in Nasal-Lavage Fluid as an Indicator of the Immediate Allergic Response".

Broide et al., (1988), *Am. Rev. Resp. Dis.,* 141:pp. 563-568, "Airway Levels of Mast Cell-Derived Mediators in Exercise-Induced Asthma".

Kalenderian et al., (1988), *Chest,* 94:pp. 119–123, "Elevated Histamine and Tryptase Levels in Smokers' Bronchoalveolar Lavage Fluid* Do Lung Mast Cells Contribute to Smokers' Emphysema".

Ruoss et al., (1991), *J. Clin. Invest.,* 88:pp. 493–499, "Mast Cell Tryptase is a Mitogen for Cultured Fibroblasts".

Wenzel et al., "Activation of Pulmonary Mast Cells by Bronchoal-veolar Allergen Challenge," *Am. Rev. Respir. Dis.,* 137: (5) pp. 1102–1108. (1987).

COMPOSITIONS AND METHODS FOR THE TREATMENT OF IMMUNOMEDIATED INFLAMMATORY DISORDERS

CROSS-REFERENCE TO RELATED APPLICATION

This application is a continuation-in-part of application Ser. No. 08/031,187, now abandoned, which is related to the subject matter of U.S. patent application Ser. No. 08/030,770, both applications filed on Mar. 12, 1993, titled "COMPOSITIONS AND METHODS FOR THE TREATMENT OF IMMUNOMEDIATED INFLAMMATORY DISORDERS" and "METHODS FOR THE TREATMENT OF HYPERRESPONSIVENESS ASSOCIATED WITH CHRONIC ASTHMA", respectively. These copending applications are expressly incorporated herein by reference.

BACKGROUND OF THE INVENTION

1. Field of the Invention

This invention relates generally to compositions and methods for the prevention and treatment of immunomediated inflammatory disorders. More particularly, the invention relates to the prevention and treatment of inflammatory diseases associated with the respiratory tract, such as asthma and allergic rhinitis. The compositions and methods of the present invention are especially useful for preventing or treating the late phase bronchoconstriction and airway hyperresponsiveness associated with chronic asthma.

2. Description of the Background Art

Asthma is a complex disease involving multiple biochemical mediators for both its acute and chronic manifestations. Asthma frequently is characterized by progressive development of hyperresponsiveness of the trachea and bronchi to both immunospecific allergens and generalized chemical or physical stimuli. The hyperresponsiveness of asthmatic bronchiolar tissue is believed to result from chronic inflammation reactions, which irritate and damage the epithelium lining the airway wall and promote pathological thickening of the underlying tissue. Bronchial biopsy studies have indicated that even patients with mild asthma have features of inflammation in the airway wall.

One initiator of the inflammatory sequence is an allergic response to inhaled allergens. Leukocytes carrying IgE receptors, notably mast cells and basophils, but also including monocytes, macrophages, and eosinophils, are present in the epithelium and underlying smooth muscle tissues of bronchi, where they are activated initially by binding of specific inhaled antigens to the IgE receptors. Activated mast cells release a number of preformed or primary chemical mediators of the inflammatory response and enzymes. Furthermore, numerous secondary mediators of inflammation are generated in situ by enzymatic reactions of activated mast cells, including superoxide and lipid derived mediators. In addition, several large molecules are released by degranulation of mast cells: proteoglycans, peroxidase, arylsulfatase B, and notably the proteases tryptase and chymotryptic proteinase (chymase). See "Drug Therapy of Asthma", Chap. 62, 1054–54.

This chemical release from mast cells probably accounts for the early bronchiolar constrictor response that occurs in susceptible individuals after exposure to airborne allergens. The early asthmatic reaction is maximal at around fifteen minutes after allergen exposure; recovery occurs over the ensuing one to two hours. In 25–35% of individuals, the early asthmatic reaction is followed by a further decline in respiratory function which begins within a few hours and is maximal between six and twelve hours post-exposure. This late asthmatic reaction is accompanied by a marked increase in the number of inflammatory cells infiltrating bronchiolar smooth muscle and epithelial tissues, and spilling into the airways. These cells include eosinophils, neutrophils, and lymphocytes, all of which are attracted to the site by release of mast cell derived chemotactic agents. The infiltrating cells themselves become activated during the late reaction phase. The late asthmatic response is believed to be a secondary inflammatory reaction mediated in part by the secretory activity of macrophages.

A related set of inflammatory reactions occurs in the upper respiratory tract mucosa, usually in response to airborne allergens. As in asthma, mast cells are activated by crosslinking of IgE molecules to particular antigens. In allergic, perennial or vasomotor rhinitis, mast cells may be activated in the absence of discernible exposure to a particular antigen. In either case, activated mast cells release primary and secondary mediators of inflammation upon degranulation. Eosinophils and macrophages are attracted to the site to perpetuate the inflammation reaction. Nasal epithelial tissue destruction often occurs in late-phase reactions.

Tryptase is the major secretory protease of human mast cells and is proposed to be involved in neuropeptide processing and tissue inflammation. Mature human tryptase is a glycosylated, heparin-associated tetramer of heterogenous, catalytically active subunits. The tryptase monomer's amino acid sequence, like its gene structure, has no close counterpart among the numerous other serine proteinases that have been characterized. See, e.g., Vanderslice et al. (1990) *Proc. Natl. Acad. Sci. USA* 87:3811–3815; Miller et al. (1990) *J. Clin. Invest.* 86:864–870; Miller et al. (1989) *J. Clin. Invest.* 84:1188–1195; and Vanderslice et al. (1989) *Biochemistry* 28:4148–4155.

Tryptase is stored in mast cell secretory granules. After mast cell activation, human tryptase can be measured readily in a variety of biologic fluids. For example, after anaphylaxis, tryptase appears in the bloodstream, where it remains detectable for several hours. See Schwartz et al. (1987) *N. Engl. J. Med.* 316:1622–1626. Its appearance has been detected in samples of nasal and lung lavage fluid from atopic subjects challenged with specific antigen. See Castells and Schwartz 1988) *J. Allerg. Clin. Immunol.* 82:348–355 and Wenzel et al. (1988) *Am. Rev. Reap. Dis.* 141:563–568. Tryptase levels in lung lavage fluid obtained from atopic asthmatics increase after endobronchial allergen challenge. Id. Some smokers of cigarettes have striking elevations of bronchoalveolar lavage fluid tryptase levels compared to nonsmoking controls, a finding that provides some support for the hypothesis that release of proteinases from activated mast cells could contribute to lung destruction in smoker's emphysema. See Kalenderian et al. (1988) *Chest* 94:119–123. In addition, tryptase has been shown to be a potent mitogen for fibroblasts, suggesting its involvement in pulmonary fibrosis and interstitial lung diseases. See Ruoss et al. (1991) *J. Clin. Invest.* 88:493–499.

Tryptase has been implicated in a variety of biological processes, including degradation of vasodilating and bronchorelaxing neuropeptides (see Caughey et al. (1988) *J. Pharmacol. Exp. Ther.* 244:133–137; Franconi et al. (1988) *J. Pharmacol. Exp. Ther.* 248:947–951; and Tam et al. (1990) *Am. J. Respir. Cell Mol. Biol.* 3:27–32) and modulation of bronchial responsiveness to histamine (see Sekizawa et al. (1989) *J. Clin. Invest.* 83:175–179). These studies suggest that tryptase possibly increases bronchoconstriction in asthma by destroying bronchodilating peptides.

Additionally, tryptase has been shown to cleave fibrinogen α-chains, as well as high molecular weight kininogen with a possible release of kinins and thus, may play a role with heparin as a local anticoagulant. The ability of tryptase to activate prostromelysin (pro-MMP-3) and procollagenase (pro-MMP-1) via MMP-3 suggests that tryptase also may be involved in tissue inflammation and remodeling. This finding also intimates that tryptase may play a role in joint destruction in rheumatoid arthritis. In addition, tryptase has been shown to cleave calcitonin gene-related peptide. As this peptide is implicated in neurogenic inflammation, tryptase could be a factor in the regulation of flare reaction in cutaneous neurogenic inflammation. See Caughey (1991) *Am. J. Respir. Cell Mol. Biol.* 4:387–394.

Asthma has become the most common chronic disease in industrialized countries. To date, conventional methods and therapeutic agents have not proved to be effective in the treatment of asthma or other immunomediated inflammatory disorders. For these reasons it would be desirable to provide improved compositions and methods which avoid the disadvantages of these conventional agents and methods while providing effective treatment for these diseases.

SUMMARY OF THE INVENTION

The present invention provides novel tryptase inhibitors comprising compounds of Formula I:

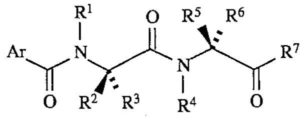

or a pharmaceutically acceptable salt thereof, wherein:

Ar is hydroxyl substituted aryl or hydroxyl substituted heteroaryl, wherein the hydroxyl is positioned ortho to the amide side chain and wherein if Ar is hydroxyl substituted aryl, the aromatic ring bearing the amide side chain is not substituted with halogen and does not bear a lower alkyl group on the position ortho to the hydroxyl;

$R^1$ is hydrogen, lower alkyl, arylalkyl, or heteroarylalkyl;

$R^2$ is hydrogen or lower alkyl;

$R^3$ is selected from the group consisting of:

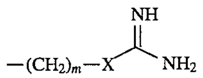

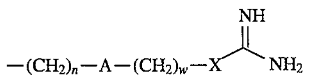

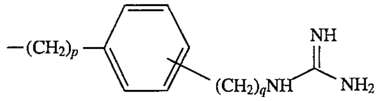

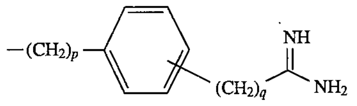

-continued

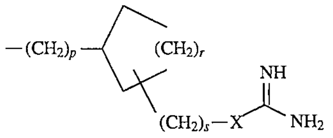

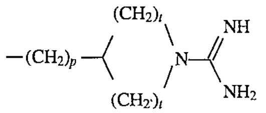

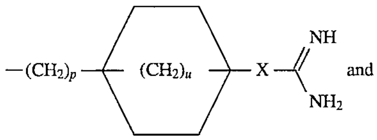 and $-(CH_2)_v-NH_2$ wherein m is an integer from 3–6, n is an integer from 0–3, p is an integer from 0–2, q is an integer from 0–2; r is an integer from 0–5; s is an integer from 0–2; t is an integer from 1–3; u is 1 or 2; v is an integer from 3–6; and w is an integer from 0–3; A is —CH=CH— or —C≡C—; and X is —NH— or —$CH_2$—;

$R^4$ is lower alkyl, substituted arylalkyl or substituted heteroarylalkyl and $R^5$ and $R^6$ are independently selected from the group consisting of hydrogen, lower alkyl, substituted arylalkyl, and substituted heteroarylalkyl; or $R^4$and $R^5$ together with the nitrogen and carbon to which they are attached, form a substituted 4-membered, 5-membered, or 6-membered heterocycle and $R^6$ is hydrogen; or $R^4$ and $R^6$ together with the nitrogen and carbon to which they are attached, form a substituted 4-membered, 5-membered, or 6-membered heterocycle and $R^5$ is hydrogen; and $R^7$ is —$OR^8$ or —$NR^8R^9$, wherein $R^8$ and $R^9$ are independently selected from the group consisting of hydrogen, lower alkyl, aryl, arylalkyl, or heteroarylalkyl or $R^8$ and $R^9$ together with the nitrogen to which they are attached, form a substituted 5-membered or 6-membered heterocycle.

In a preferred embodiment, Ar is 1-hydroxy-2 -naphthyl, 2-hydroxyl-1-naphthyl, 3-hydroxy-2-pyridyl, or 2 -hydroxy-3-quinoxalyl; $R^1$ is hydrogen; $R^2$ is hydrogen; $R^3$ is selected from the group consisting of:

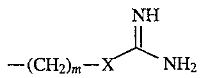

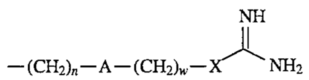

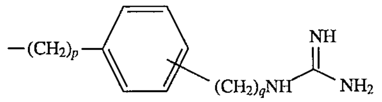

and

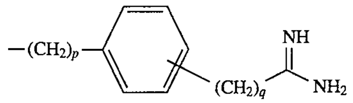

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

either $R^4$ is lower alkyl and $R^5$ and $R^6$ are hydrogen; or $R^4$ and $R^5$, together with the nitrogen and carbon to which they are attached form a substituted 4-membered, 5-membered, or -membered heterocycle and $R^6$ is hydrogen; and $R^7$ is —OH, —$OCH_3$, —$NH_2$, 3'-aminocarboxy-1'-piperidyl, or —$N(CH_3)_2$.

A particularly preferred tryptase inhibitor of Formula I is Compound 3 of Tables I and II:

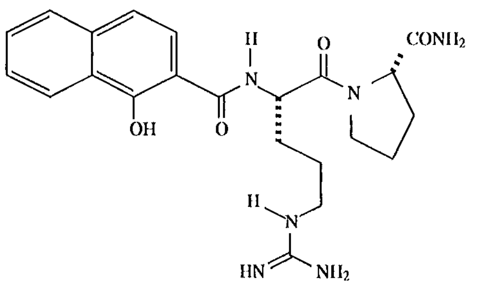

Another preferred tryptase inhibitor of Formula I is Compound 15 of Tables I and II:

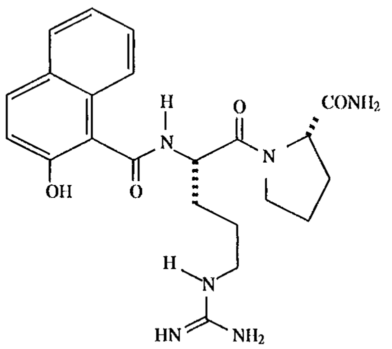

The compounds described herein are useful for the prevention and treatment of immunomediated inflammatory disorders, and particularly those associated with the respiratory tract, including asthma, and particularly the hyperresponsiveness phase associated with chronic asthma, and allergic rhinitis. Thus, the present invention also provides a method for treating immunomediated inflammatory disorders wherein a patient having an immunomediated inflammatory disorder that is susceptible to treatment with a tryptase inhibitor receives, or is administered, a therapeutically effective dose or amount of a compound of the present invention.

The invention also provides for pharmaceutical compositions of the compounds described herein. These pharmaceutical compositions can be in a variety of forms including oral dosage forms, as well as injectable and infusible solutions. Typically, when used for the treatment or prevention of the asthma, and particularly the hyperresponsiveness associated with chronic asthma, these pharmaceutical compositions are in an aerosol form of powders or solutions. When used for the treatment of immunomediated inflammatory skin conditions, the compounds of the instant invention are used in combination with a non-toxic, pharmaceutically acceptable topical carrier. The compounds of the instant invention can be used in combination with antiinflammatories or other asthma therapies, such as β-adrenergic agonists, antiinflammatory corticosteroids, anticholinergics, and the like.

DESCRIPTION OF SPECIFIC EMBODIMENTS

I. Definitions and General Parameters

Figure 1:
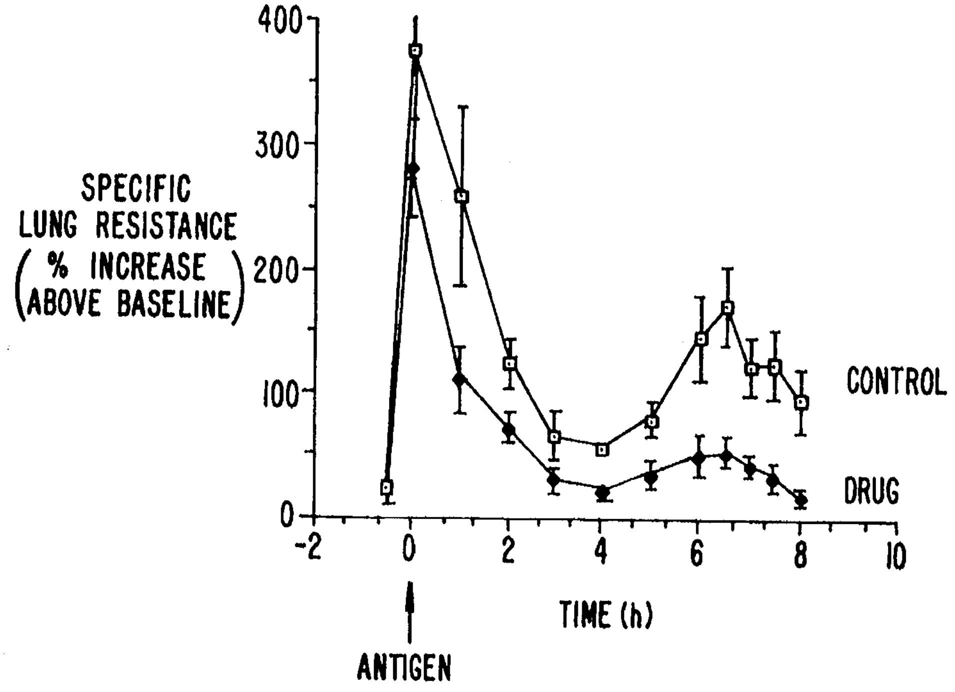
FIG. 1 is a graph showing specific lung resistance in sheep as a function of time in hours post-antigen challenge. Open squares indicate control values, and filled circles indicate values for the same animal after administration of Compound 3 of Tables I and II.

The following definitions are set forth to illustrate and define the meaning and scope of the various terms used to describe the invention herein.

"Immunomediated inflammatory disorder" includes generally those diseases associated with mast cell mediator release and susceptible to treatment with a tryptase inhibitor. Examples of such disorders include diseases of immediate type hypersensitivity such as asthma, allergic rhinitis, urticaria and angioedema, and eczematous dermatitis (atopic dermatitis), and anaphylaxis, as well as hyperproliferative skin disease, peptic ulcers, inflammatory bowel disorder, inflammatory skin conditions, and the like.

"Hyperresponsiveness" refers to late phase bronchoconstriction and airway hyperreactivity associated with chronic asthma. Hyperresponsiveness of asthmatic bronchiolar tissue is believed to result from chronic inflammation reactions, which irritate and damage the epithelium lining the airway wall and promote pathological thickening of the underlying tissue.

"Halogen" refers to fluorine, bromine, chlorine, and iodine atoms.

"Hydroxyl" refers to the group —OH.

"Lower alkyl" refers to a branched or straight chain alkyl group of one to six carbon atoms. This term is further exemplified by such groups as methyl, ethyl, n-propyl, i-propyl, n-butyl, t-butyl, i-butyl (or 2 -methylpropyl), i-amyl, n-amyl, and hexyl.

"Cycloalkyl" refers to a carbocyclic hydrocarbon group of three to six carbon atoms. The term is exemplified by such groups as cyclopropylmethyl and cyclohexyl.

"Aryl" or "Ar" refers to an aromatic carbocyclic group having a single ring (e.g., phenyl), multiple rings (e.g., biphenyl) or multiple condensed rings in which at least one ring is aromatic, (e.g., 1,2,3,4-tetrahydronaphthyl, naphthyl, anthryl, or phenanthryl), which can optionally be unsubstituted or substituted with, selected from the group consisting of halogen, lower alkyl, lower alkoxy, lower alkylthio, trifluoromethyl, lower acyloxy, aryl, heteroaryl and hydroxy. However, according to the instant invention, the aromatic ring bearing the amide side chain cannot be further substituted with halogen. In addition, the aromatic ring bearing the amide side chain cannot possess a lower alkyl group ortho to the hydroxyl group (i.e., meta to the amide side chain).

"Heterocycle" refers to a saturated, unsaturated, or aromatic carbocyclic group having a single ring (e.g., morpholino, pyridyl or furyl) or multiple condensed rings (e.g., naphthyridinyl, quinoxalyl, quinolinyl, indolizinyl or benzo [b]thienyl) and having at least one hetero atom, such as N, O or S, within the ring, which can optionally be unsubstituted or substituted with, selected from the group consisting of halogen, lower alkyl, lower alkoxy, lower alkylthio, trifluoromethyl, lower acyloxy, and hydroxy. The term "heteroaryl" or "HetAr" refers to a heterocycle in which at least one heterocyclic ring is aromatic.

"Arylalkyl" refers to the group -R-Ar where Ar is an aryl group and R is straight-chain or branched-chain aliphatic group. Arylalkyl groups can optionally be unsubstituted or substituted with, selected from the group consisting of halogen, lower alkyl, lower alkoxy, lower alkylthio, trifluoromethyl, lower acyloxy, and hydroxy.

"Heteroarylalkyl" refers to the group -R-HetAr where HetAr is an heteroaryl group and R is straight-chain or branched-chain aliphatic group. Heteroarylalkyl groups can optionally be unsubstituted or substituted with, selected from the group consisting of halogen, lower alkyl, lower alkoxy, lower alkylthio, trifluoromethyl, lower acyloxy, and hydroxy.

"Pharmaceutically acceptable salt" refers to those salts which retain the biological effectiveness and properties of the parent compound and which are not biologically or otherwise undesirable.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

"Treatment" or "treating" refers to any administration of a tryptase inhibitor in vitro or in vivo and includes:

(i) inhibiting the symptoms of the disease;

(ii) lessening or inhibiting the long term effects of the disease; and/or (iii) relieving the symptoms of the disease.

II. Tryptase Inhibitors

The present invention provides compositions comprising an effective serine protease inhibitor, and more particularly a tryptase inhibitor, that is useful for reducing immunomediated-inflammatory disorders, and particularly bronchoconstriction induced by allergenic challenge in an asthmatic animal.

Tryptase inhibitors are substances which slow down or prevent tryptase activity. According to one aspect of the present invention, the tryptase inhibitors will comprise a compound of Formula I:

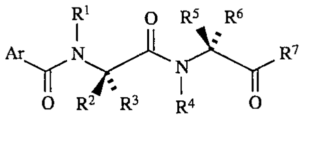

or a pharmaceutically acceptable salt thereof, wherein:

Ar is hydroxyl substituted aryl or hydroxyl substituted heteroaryl, wherein the hydroxyl is positioned ortho to the amide side chain and wherein if Ar is hydroxyl substituted aryl, the aromatic ring bearing the amide side chain is not substituted with halogen and does not bear a lower alkyl group on the position ortho to the hydroxyl;

$R^1$ is hydrogen, lower alkyl, arylalkyl, or heteroarylalkyl;

$R^2$ is hydrogen or lower alkyl;

$R^3$ is selected from the group consisting of:

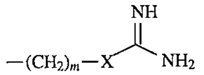

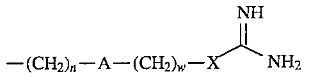

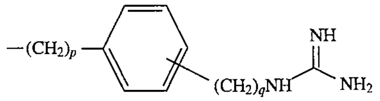

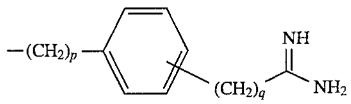

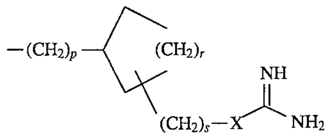

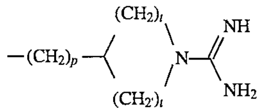

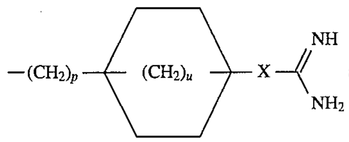 and $-(CH_2)_v-NH_2$ wherein m is an integer from 3–6, n is an integer from 0–3, p is an integer from 0–2, q is an integer from 0–2; r is an integer from 0–5; s is an integer from 0–2; t is an integer from 1–3; u is 1 or 2; v is an integer from 3–6; and w is an integer from 0–3; A is —CH=CH— or —C≡C—; and X is —NH— or —$CH_2$—;

$R^4$ is lower alkyl, substituted arylalkyl, or substituted heteroarylalkyl and $R^5$, and $R^6$ are independently selected from the group consisting of hydrogen, lower alkyl, substituted arylalkyl, and substituted heteroarylalkyl; or $R^4$ and $R^5$ together with the nitrogen and carbon to which they are attached form a substituted 4-membered, 5-membered, or 6-membered heterocycle and $R^6$ is hydrogen; or $R^4$ and $R^6$ together with the nitrogen and carbon to which they are attached form a substituted 4-membered, 5-membered, or -membered heterocycle and $R^5$ is hydrogen; and $R^7$ is —$OR^8$ or —$NR^8R^9$, wherein $R^8$ and $R^9$ are independently selected from the group consisting of hydrogen, lower alkyl, aryl, arylalkyl, or heteroarylalkyl or $R^8$ and $R^9$ together with the nitrogen to which they are attached, form a substituted 5-membered or 6-membered heterocycle.

In a preferred embodiment, Ar is 1-hydroxy-2 -naphthyl, 2-hydroxyl-1-naphthyl, 3-hydroxy-2-pyridyl, or 2 -hydroxy-3-quinoxalyl; $R^1$ is hydrogen; $R^2$ is hydrogen; $R^3$ is selected from the group consisting of:

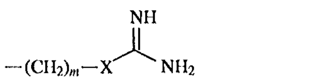

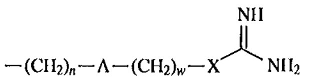

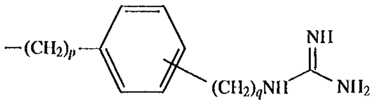

and

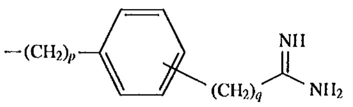

wherein m is an integer from 3–6, n is an integer from 0–3, p is an integer from 0–2, q is an integer from 0–2; and w is an integer from 0–3; A is $-CH{=}CH-$ or $-C{\equiv}C$; and X is $-NH-$ or $-CH_2-$;

either $R^4$ is lower alkyl and $R^5$ and $R^6$ are hydrogen; or $R^4$ and $R^5$ together with the nitrogen and carbon to which they are attached form a substituted 4-membered, 5-membered, or 6-membered heterocycle and $R^6$ is hydrogen; and $R^7$ is $-OH$, $-OCH_3$, $-NH_2$, -3'-aminocarboxy-1'-piperidyl, or $-N(CH_3)_2$.

A preferred tryptase inhibitor is Compound 3 of Tables I and II:

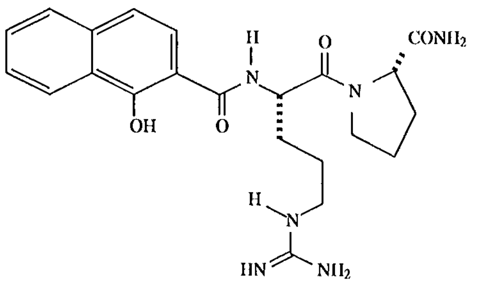

An additional preferred tryptase inhibitor is Compound 15 of Tables I and II:

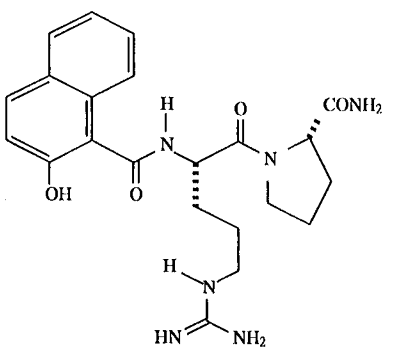

Another preferred tryptase inhibitor is Compound 21 of Tables I and II:

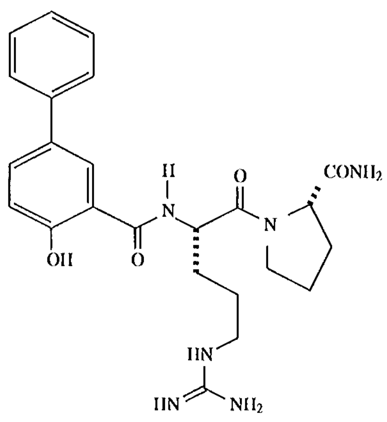

The tryptase inhibitors of the present invention can be obtained by known techniques from readily available starting materials, as described in greater detail below.

Compounds of this invention can, depending on the nature of the functional groups, form addition salts with various inorganic and organic acids and bases. These salts can be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Salts can also be formed from a carboxylic acid residue via treatment with alkali metals or alkali metal bases, such as alkali metal hydroxides and alkali metal alkoxides, or alkaline earth metals or alkaline earth metal bases, such as alkaline earth metal hydroxides and alkaline earth metal alkoxides. In addition, salts can be formed from a carboxylic acid and an organic base, such as trimethylamine, diethylamine, ethanolamine, piperidine, isopropylamine, choline, caffeine, and the like.

The salts can be formed by conventional means, as by reacting the free acid or base forms of the product with one or more equivalents of the appropriate base or acid in a solvent or medium in which the salt is insoluble, or in a solvent such as water, which is then removed in vacuo or by freeze-drying or by exchanging the cations of an existing salt for another cation on a suitable ion exchange resin.

III. In Vitro and In Vivo Testing

In vitro protocols for screening potential inhibitors as to their ability to inhibit tryptase are known in the art. See, e.g., Sturzebecher et al. (1992) *Biol. Chem. Hoppe-Seyler* 373:1025–1030. Typically, these assays measure the tryptase-induced hydrolysis of peptide-based chromogenic substances. Details of an exemplary procedure are described below.

In addition, the activity of the compounds of the present invention can be evaluated in vivo in one of the numerous animal models of asthma. See Larson, "Experimental Models of Reversible Airway Obstruction", in *The Lung: Scientific Foundations*, Crystal, West et al., eds., Raven Press, New York, 1991; Warner et al. (1990) *Am. Rev. Respir. Dis.* 141:253–257. An ideal animal model would duplicate the chief clinical and physiological features of human asthma, including: airway hyperresponsiveness to chemical mediators and physical stimuli; reversal of airway obstruction by drugs useful in human asthma (β-adrenergics, methylxanthines, corticosteroids, and the like); airway inflammation with infiltration of activated leukocytes; and chronic inflammatory degenerative changes, such as basement membrane thickening, smooth muscle hypertrophy, and epithelial damage. Species used as animal models include mice, rats, guinea pigs, rabbits, dogs, and sheep. All have some limitations, and the proper choice of animal model depends upon the question which is to be addressed.

The initial asthmatic response can be evaluated in guinea pigs, and dogs, and particularly, with a basenji-greyhound cross strain which develops nonspecific airway hyperresponsiveness to numerous nonallergenic substances, such as methacholine and citric acid. Certain selected sheep exhibit a dual response after antigen challenge with Ascaris proteins. In dual responding animals, the initial asthmatic response (IAR) is followed by a late asthmatic response (LAR) at 6–8 hours post-exposure. Hypersensitivity to the cholinergic agonist carbachol increases at 24 hours after antigen challenge in those animals which exhibit LAR.

The allergic sheep model was used to evaluate the potential antiasthmatic effects of the compounds of the present invention. Administration of compositions comprising aerosolized solutions of the compounds of the instant invention to allergic sheep prior to or following exposure to specific allergens demonstrates that such compositions substantially lessen or abolish the late asthmatic response and consequent hyperresponsiveness.

The compounds of this invention are also useful for the treatment of other immunomediated inflammatory disorders in which tryptase activity contributes to the pathological condition. Such diseases include inflammatory diseases associated with mast cells, such as rheumatoid arthritis, rheumatoid spondylitis, osteoarthritis, gouty arthritis and other arthritic conditions, inflammatory bowel disease, peptic ulcer and various skin conditions.

The efficacy of the compounds of the instant invention for the treatment of the vast majority of immunomediated inflammatory disorders can be evaluated by either in vitro or in vivo procedures. Thus, the anti-inflammatory efficacy of the compounds of the instant invention can be demonstrated by assays well known in the art, for example, the Reversed Passive Arthus Reaction (RPAR)-PAW technique (see, e.g., Ganguly et al. (1992) U.S. Pat. No. 5,126,352). Assays for determining the therapeutic value of compounds in the treatment of various skin conditions, such as hyperproliferative skin disease, are well known in the art, for example, the Arachidonic Acid Mouse Ear Test (id). The compounds of the instant invention can be evaluated for their antiulcer activity according to the procedures described in Chiu et al. (1984) *Archives Internationales de Pharmacodynamie et de Therapie* 270:128–140.

IV. In Vivo Administration

According to this invention, a therapeutically or pharmaceutically effective amount of a tryptase inhibitor and particularly, a compound of Formula I, is administered to a patient suffering from an immunomediated inflammatory disorder. According to one embodiment, the compositions of the present invention are useful for preventing or ameliorating asthma. In using the compositions of the present invention in a treatment of asthma, the compounds may be administered prophylactically prior to exposure to allergen or other precipitating factor, or after such exposure. The compounds of the instant invention are particularly useful in ameliorating the late-phase tissue destruction seen in both seasonal and perennial rhinitis. Another aspect of the present invention is directed to the prevention and treatment of other immunomediated inflammatory disorders associated with mast cells such as urticaria and angioedema, and eczematous dermatitis (atopic dermatitis), and anaphylaxis, as well as hyperproliferative skin disease, peptic ulcers, and the like.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity and course of the disease, previous therapy, the patient's health status and response to the drugs, and the judgment of the treating physician.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the tryptase inhibitor will be in the range of 0.1 to 1000 milligram (mg) per recipient per day, preferably in the range of 1 to 100 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form.

The composition used in these therapies can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application.

While it is possible to administer the active ingredient of this invention alone, it is preferable to present it as part of a pharmaceutical formulation. The formulations of the present invention comprise at least one compound or inhibitor of this invention in a therapeutically or pharmaceutically effective dose together with one or more pharmaceutically or therapeutically acceptable carriers and optionally other therapeutic ingredients. Various considerations are described, e.g., in Gilman et al. (eds) (1990) *Goodman and Gilman's: The Pharmacological Bases of Therapeutics,* 8th Ed., Pergamon Press; and *Remington's* supra. Methods for administration are discussed therein, e.g., for oral, intravenous, intraperitoneal, or intramuscular administration, and others. Pharmaceutically acceptable carriers will include water, saline, buffers, and other compounds described, e.g., in the Merck Index, Merck & Co., Rahway, N.J.

Typically, when the compounds of the instant invention are to be used in the treatment of asthma or allergic rhinitis, they will be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the present invention, the preferred range of concentration of the compounds of the instant invention is 0.1–100 milligrams (mg)/milliliter (mL), more preferably 0.1–30 mg/mL, and most preferably, 1–10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

Solutions of the compounds of the instant invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the instant invention connected to or contained within any of the conventional means for creating aerosols in asthma medication, such as metered dose inhalers, jet nebulizers, or ultrasonic nebulizers. Optionally such device may include a mouthpiece fitted around the orifice.

In an embodiment for the treatment of allergic rhinitis, a device may comprise a solution of a compound of the instant invention in a nasal sprayer.

A dry powder comprising a compound of the instant invention, optionally with an excipient, is another embodiment of the present invention. This may be administered by a drug powder inhaler containing the above described powder.

It should, of course, be understood that the methods of this invention can be used in combination with other agents for the treatment of immunomediated inflammatory disorders, and particularly asthma. β-Adrenergic agonists are especially useful in these combinations, because they provide symptomatic relief of the initial asthmatic response, whereas the compounds of the present invention provide relief for the late asthmatic response. Preferred β-adrenergic agonists in these solutions include any of the usual β-agonists employed for the relief of asthma, such as albuterol, terbutaline, formoterol, fanoterol, or prenaline.

Other agents useful in combination with the compounds of the instant invention include anticholinergics, such as ipratropium bromide, and antiinflammatory corticosteroids (adrenocortical steroids) such as beclomethasone, triamcinolone, flurisolide, or dexamethasone.

The compounds of the inventions can also be used in the treatment of immunomediated inflammatory skin conditions, such as urticaria and angioedema, eczematous dermatitis, and hyperproliferative skin disease, e.g., psoriasis, in mammals. As a result of the topical administration of a compound of Formula I, a remission of the symptoms can be expected. Thus, one affected by an immunomediated inflammatory skin condition can expect a decrease in scaling, erythema, size of the plaques, pruritus, and other symptoms associated with the skin condition. The dosage of medicament and the length of time required for successfully treating each individual patient may vary, but those skilled in the art will be able to recognize these variations and adjust the course of therapy accordingly.

Also included within the invention are preparations for topical application to the skin comprising a compound of Formula I, typically in concentrations in the range of from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

The compounds of this invention are also useful in the treatment of peptic ulcers. More specifically, they display chemotherapeutic activity which enables them to relieve the symptoms of peptic ulcer disease and stress ulceration, and to promote the healing of gastric and/or duodenal ulcers. The compounds can be used in conjunction with other therapeutic agents, such as anti-inflammatory and/or analgesic agents, such as aspirin, indomethacin, phenylbutazone, ibuprofen, naproxen, tolemtim, and the like.

The pharmaceutical compositions can be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions can be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. These compositions will sometimes be sterilized by conventional, well known sterilization techniques, or can be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

In order that the invention described herein can be more fully understood, the following examples are set forth. It should be understood that these examples are for illustrative purposes only, and are not to be construed as limiting this invention in any manner.

EXPERIMENTAL

I. General

Starting materials not described herein are available commercially, are known, or can be prepared by methods known in the art. Compounds of Formula I can be prepared by techniques known in the art using either solid phase or solution phase synthesis techniques. Starting materials for the preparation of compounds of Formula I are known in the art or can be prepared by methods well known to those skilled in the art. For example, techniques for solid phase synthesis of polypeptides are described, for example, in *Solid Phase Peptide Synthesis: A Practical Approach,* (eds. E. Atherton and R. C. Sheppard) IRL Press at Oxford University Press (1989) and in Merrifield, *J. Amer. Chem. Soc.* 85:2149–2156 (1963). Peptide coupling chemistry is also described in *The Peptides*, Vol. 1, (eds. Gross, E., and J. Meienhofer), Academic Press, Orlando (1979). Other techniques include those of Geysen et al., *J. Imm. Meth.*, (1987) 102:259–274; Houghten et al., *Nature* (1991) 354:84–86.

In the process described herein for the preparation of compounds of this invention, the requirements for protecting groups are generally well recognized by one skilled in the art of organic chemistry. Accordingly, the use of appropriate protecting groups is necessarily implied by the processes contained herein, although not expressly illustrated.

Isolation and purification of the compounds and intermediates described herein can be effected, if desired, by any suitable separation or purification procedure such as, for example, filtration, extraction, crystallization, column chromatography, thin-layer chromatography or thick-layer chromatography, high-pressure liquid chromatography, or a combination of these procedures. Specific illustrations of suitable separation and isolation procedures can be had by reference to the examples hereinbelow. However, other equivalent separation or isolation procedures can, of course, also be used.

The Sakaguchi assay was for the detection of arginine and peptides containing arginine. See Stewart and Young "Solid Phase Peptide Synthesis" 2d Ed Pierce Chemical Company, p 114. Solution I containing 0.01% α-naphthol and 5% urea in 95% ethanol was prepared. Solution II was prepared by dissolving 2 gram (g) bromine in 100 milliliters (mL) of 8% aqueous sodium hydroxide. To Solution I was added 5 sodium hydroxide pellets. The sample to be analyzed was spotted on a thin layer chromatography (TLC) plate. The TLC plate was then sprayed with Solution I. The TLC plate was dried in air and then sprayed with solution II. A red spot indicated the existence of an aminoimino methane group.

II. Solid Phase Synthesis of Compounds of Formula I

A. Preparation of Compound 3 of Tables I and II 4-(2',4'-Dimethoxyphenyl-fluorenylmethyloxycarbonyl (Fmoc)-aminomethyl)-phenoxy resin (Rink resin; Bachem, CA; 3.5 grams (g) at a loading of 0.289 milliequivalent/gram (meq/g), 1.01 millimoles (mmol)) was suspended in 30 milliliters (mL) of a 1:1 solution (volume/volume (v/v)) of N,N-dimethylformamide (DMF):toluene containing 30% (by volume) piperidine. The reaction mixture was agitated for 5 minutes and was then filtered. Additional piperidine solution (30 mL) was added and the mixture was agitated for an additional 5 minutes. After filtration, the resin beads were washed sequentially with DMF (6×) and methylene chloride (6×).

Fmoc-L-proline (Milligen; 6.06 mmol), benzotriazole-1-yl-oxy-tris-(dimethylamino)-phosphonium hexafluorophosphate (BOP, Novabiochem; 6.06 mmol), and 1-hydroxybenzotriazole (HOBT; Aldrich; 6.06 mmol) were dissolved in -30 mL of DMF. The resulting clear solution was added to the Rink resin and the slurry was agitated (with nitrogen bubbling) for 4 hours. The reaction mixture was filtered and the resin beads were washed as described above. The Fmoc group was removed with piperidine as described above.

A solution of Fmoc-L-arginine(PMC) (Milligen; 6.06 mmol), BOP (6.06 mmol), and HOBT (6.06 mmol) in DMF (30 mL) was added to the resin beads and the slurry was agitated for 4 hours and was then filtered, washed, treated with piperidine, and washed again as described above.

A solution of 1-hydroxy-2-naphthoic acid (Aldrich; 1.14 gm, 6.06 mmol), 1,3-diisopropylcarbodiimide (DIPCDI; Aldrich; 0.949 mL, 6.06 mmol) and HOBT (0.819 g, 6.06 mL) in DMF (45 mL) was added and the reaction mixture was agitated (mechanical rocker arm) for 7 hours. After filtration, washing and piperidine treatment (described above), the resin was washed sequentially with DMF (6×), methylene chloride (6×) and methanol (6×). The resin was suspended in methanol and agitated (mechanical rocker arm) overnight (15 hours). The resin was filtered and washed twice with methanol.

The white, free flowing solid was then suspended in a solution of trifluoroacetic acid (TFA):anisole:water (90:5:5, 30 mL). The resin immediately turned pink and then darkened over the course of 1–2 minutes to a deep red color. After agitating for 5 minutes the reaction mixture was filtered. This procedure was repeated 2 additional times with fresh cleavage reagent, except that contact time was increased to 10 minutes for each iteration.

The TFA solutions were combined and the resulting clear, orange solution was allowed to sit at room temperature for 3.5 hours. Concentration in vacuo afforded a pale yellow oil which was kept in vacuo (<1 torr) for 3 hours. The oil was dissolved in 50% aqueous acetonitrile (100 mL) and lyophilized to afford the crude product as an off-white solid (471 mg).

Analytical HPLC (Polymer Labs 100A PLRP column, 1.0×150 millimeters (mm), eluting with a linear gradient of 20 to 45% acetonitrile over 13 minutes at a flow of 0.1 mL/min) showed that the crude product was essentially a single compound (retention time 10.35 minutes, >98% by UV absorbance). Purification was accomplished via HPLC using a $C_{18}$ silica gel column (Vydac; 22×250 mm, 15–20 μm, 300 A, eluting with a linear gradient of 20 to 35% over 30 minutes at a flow of 10 mL/minute). Multiple injections of 30–35 mg were required. Like fractions (retention time~44–48 minutes) were combined and lyophilized to afford a fluffy white solid (351 mg) which was a single compound by HPLC.

Electrospray mass spectroscopy (calculated molecular weight=440.49, found $M^{+1}$=441.1) and NMR spectroscopy (proton and $^{13}C$) are consistent with the expected structure. $^1H$ NMR ($CD_3OD$) δ7.89 (d, J=8 Hz, 1H), 7.78 (d, J=6 Hz, 1H), 7.76 (d, J=6 Hz, 1H), 7.57 (dt, J=8, 1 Hz, 1H), 7.48 (dt, J=8, 1 Hz, 1H), 7.29 (d, J=8 Hz, 1H), ~4.95 (obscured, 1H), 4.49 (dd, J=8, 5 Hz, 1H), 3.97 (dt, J=10, 7 Hz, 1H), 3.73 (dt, J=10, 7 Hz, 1H), 3.23 (t, J=7 Hz, 2H), 2.29 (m, 1H), 1.7–2.2 (m, 8H).

B. Preparation of Other Compounds of Formula I

By following the procedure of Part A above and substituting for 1-hydroxy-2-naphthoic acid the following compounds:

2-hydroxy-4-methylbenzoic acid;

3-hydroxy-2-quinoxalinecarboxylic acid;

3-hydroxy-2-naphthoic acid;

2-hydroxy-1-naphthoic acid;

3-hydroxy-2-pyridinecarboxylic acid;

4-hydroxy-7-methyl-3-naphthyridinecarboxylic acid;

2-hydroxy-3-pyridinecarboxylic acid;

2-hydroxybenzoic acid;

2,5-dihydroxybenzoic acid; and 2-hydroxy-5-phenylbenzoic acid (see E below)

there were obtained the following compounds:

Compound 2 of Tables I and II;

Compound 9 of Tables I and II:

Compound 14 of Tables I and II;

Compound 15 of Tables I and II;

Compound 16 of Tables I and II;

Compound 17 of Tables I and II;

Compound 18 of Tables I and II;

Compound 19 of Tables I and II;

Compound 20 of Tables I and II; and

Compound 21 of Tables I and II.

C. Preparation of Other Compounds of Formula I

By following the procedure of Part A above and substituting Fmoc-D-proline for Fmoc-L-proline, there was obtained Compound 12 of Tables III.

D. Preparation of Additional Compounds of Formula I

Compound 13 of Tables I and II was prepared by first coupling Fmoc-L-phenylalanine to the resin in an analogous procedure to that used to couple Fmoc-L-proline in part A above. The Fmoc group was then removed and the phenylalanine was coupled to Fmoc-L-proline. The remainder of the synthesis of Compound 13 was performed using the techniques described in Part A above.

Similarly, the preparation of Compounds 6 and 7 of Tables I and II involved coupling Fmoc-piperidine-3-carboxylic acid or Fmoc-piperidine-4-carboxylic acid, respectively, to the resin, removing the Fmoc group, and then coupling Fmoc-L-proline. The remainder of the syntheses were performed as described in Part A above.

E. Preparation 2-hydroxy-5-phenylbenzoic acid 2-hydroxy-5-phenylbenzoic acid was synthesized as follows. A solution of tetrahydropyran (THP)-protected 4-phenylphenol (474 mg. 2 mmol., prepared from 4-phenylphenol by standard methods described in Green and Wuts at pp. 31-34) in anhydrous THF (5 mL) was cooled to −78° C. and treated with n-Butyllithium (2 mL of 1.6M in hexanes). The reaction mixture was stirred and warmed to ambient temperature during which a tan suspension formed. After 2 hours, the reaction mixture was cooled to −78° C. and treated with excess anhydrous $CO_2$ for several minutes. The reaction mixture was stirred and warmed to ambient temperature. After 2 hours, the reaction mixture was partitioned between ethyl ether and aqueous 1N NaOH. The aqueous layer was cooled to 0° C. with ice and acidified to pH 2 with aqueous 1N HCl. The aqueous solution was partitioned with methylene chloride. The organic layer was dried over magnesium sulfate. Concentration in vacuo yielded crude product as an off-white solid (258 mg, 2-hydroxy-5-phenylbenzoic acid). NMR spectroscopy of the crude material was consistent with the expected structure. 1H NMR (DMSO-d6) δ8.04 (d, J=3 Hz, 1H), 7.76 (dd, J=9, 3 Hz, 1H), 7.62 (d, J=7 Hz, 2H), 7.44 (t, J=7 Hz, 2H), 7.32 (t, J=7 Hz, 1H), 7.00 (d, J=9 Hz, 1H). Mass calculated: 466.5. Mass found 467.2. LC Gradient 25–45% acetonitrile over 13 minutes. LC retention time 3.5 minutes. The material was used without further purification.

III. Solution Phase Synthesis of Compounds of Formula I

A. Preparation of Compound 10 of Tables I and III

To 20 g of (L)-phenylalanine cooled to −5° C. in a salt/ice bath was added 74 mL concentrated sulfuric acid. The temperature of the reaction mixture was allowed to equilibrate and then 9.4 mL of concentrated nitric acid was added dropwise over five minutes. The reaction mixture was stirred for 30 minutes and was then added to 700 mL of crushed ice/water. The pH was adjusted to 8–9 with concentrated ammonium hydroxide. The solution was allowed to crystallize at room temperature and was then cooled overnight at 4° C.. The light yellow crystalline product was collected over hardened filter paper, washed with cold water, and dried. The product was recrystallized in hot water and the filtrate was evaporated and recrystallized (2×) with an overall yield of 55%. MP: 218°–222° C. (crude). TLC: $R_f$ $(F)_{0.18}$. NMR: ($D_2O$/NaOD), γ2.99 (dd, J=13.4, 7.2 Hz, 1H), 3.10 (dd, J=13.4, 6.0 Hz, 1H), 3.57 (dd, J=7.2, 6.0 Hz, 1H), 7.48 (d, J=8.6 Hz, 2H), 8.21 (d, J=8.7 Hz, 2H).

t-Butyoxylcarbonyl (BOC)-protected amino acids can be prepared using standard techniques. See, e.g., Greene and Wuts *Protective Groups in Organic Synthesis*, 2nd Ed., John Wiley & Sons, Inc.: New York, pp. 327–328 (1991).

To a −20° C. solution of BOC-protected p-nitrophenylalanine (3.00 g, 9.67 mmol) in anhydrous methylene chloride (5 mL) was added N-methylmorpholine (NMM, 1.07 mL, 9.67 mmol), followed by isobutyl chloroformate (1.26 mL, 9.67 mmol). The reaction mixture was stirred for 15 minutes at −20° C. To the mixture was then added methyl L-proline hydrochloride (L-Pro-OMe, 1.60 g, 9.67 mmol) as a solid, followed by additional NMM (1.07 mL, 9.67 mmol). After stirring for one hour at −20° C. and one hour at room temperature, the reaction mixture was concentrated in vacuo and was then diluted with ethyl acetate. The ethyl acetate solution was washed with 10% aqueous citric acid, water, and brine, dried over magnesium sulfate, and concentrated in vacuo. Column chromatography yielded 2.4 g of product (>60% yield).

The BOC group was removed by treatment with HCl in dioxane using standard conditions. See, e.g., Greene and Wuts, id at 328–329. To a solution of 1-hydroxy-2-naphthoic acid (160 mg, 0.84 mmol) in methylene chloride and N,N-dimethylformamide (1:1, 3 mL) was added 1-hydroxybenzotriazole (159 mg, 1.17 mmol). The solution was cooled to 0° C. and 1-(3 -dimethylaminopropyl)-3-ethylcarbodiimide hydrochloride (EDCI, 161 mg, 0.84 mmol) was added. After the solution was stirred for 45 minutes at 0° C., a solution of the dipeptide (300 mg, 0.84 mmol) prepared above was added, followed by NMM (93 μl, 0.84 mmol). The reaction mixture was stirred for one hour at 0° C. and 45 minutes at room temperature. The reaction mixture was concentrated in vacuo and diluted with ethyl acetate and water. The organic layer was separated, washed (4×) with water and then brine, dried, and concentrated in vacuo. Chromatography yielded the coupled product (300 mg, 73%).

To a solution of the coupled product (410 mg, 0.83 mmol) in ethyl acetate (20 mL) was added glacial acetic acid (10 drops) and 10% palladium on activated carbon (100 mg). This solution was hydrogenated for five hours. The reaction mixture was then filtered over celite and the solution was concentrated in vacuo to yield 375 mg (98%) of product which was used without further purification.

To a solution of the product of the above hydrogenation reaction (200 mg, 0.45 mmol) in anhydrous methanol (10 mL) was added formamidinesulfonic acid (118 mg, 0.95 mmol, prepared by oxidation of commercially available formamidinesulfinic acid following the procedure outlined in Maryanoff et al. (1986) *J. Org. Chem.* 1882). The reaction mixture was stirred for three days. The reaction mixture was concentrated in vacuo and the product was isolated by chromatography (eluting with methanol:methylene chloride) to yield 17 mg of desired product, Compound 10 of Table III.

IV. Alternate Solution Phase Synthesis of Compounds of Formula I

A. Preparation of Compound 3 of Tables I and II

A solution of 1-benzyloxy-2-naphthoic acid (2.247 g) in thionyl chloride (15 mL) was refluxed for four hours. Excess reagent was evaporated in vacuo. The residue was diluted with anhydrous DMF (9 mL) and concentrated to about 2 mL. To this solution was added 4-dimethylaminopyridine (1.02 g). The mixture was stirred at ambient temperature over night. The resulting pyridinium complex was added to a stirred solution of nitro-L-arginine (1.77 g), tetramethylguanidine (1 mL) and lithium chloride (4.56 g) in DMF (60 mL). The mixture was stirred at ambient temperature for 48 hours. Most of the DMF was evaporated in vacuo and the residue was partitioned between 1.5 normal (N) aqueous HCl and ethyl acetate. The combined organic layers were washed with saturated aqueous sodium chloride solution and dried over magnesium sulfate. Concentration in vacuo yielded crude product (3.5 g, 1-benzyloxy-2-naphthoyl-N-nitro-L-arginine acid). TLC: $R_f$ of product is 0.22 (using silica gel plate and eluting with 10% methanol/acetic acid in chloroform). This material was used without further purification.

A solution of 1-benzyloxy-2-naphthoyl-N-nitro-L-arginine acid (150 mg) in anhydrous DMF (5 mL) was cooled to −25° C. and treated with isobutyl chloroformate (0.053 mL). The reaction mixture was stirred and warmed to room temperature. After 20 minutes, solid L-proline amide (as its HCl salt, 65.9 mg) was added. The mixture was stirred for 16 hours and was then diluted with ethyl acetate. The ethyl acetate solution was washed with 5% aqueous citric acid, saturated aqueous sodium bicarbonate, and saturated aqueous sodium chloride and dried over magnesium sulfate. The solution was concentrated in vacuo and the residue was diluted in ethanol (40 mL, containing 10% methanol and 10% acetic acid) and hydrogenated at 52 pounds per square inch (psi) over 10% palladium on carbon (10 mg) until the reaction was complete (TLC on silica gel, eluting with chloroform:methanol 9:1) as indicated by disappearance of the faster moving spot. The reaction mixture was filtered through celite, washed with ethanol and methanol. The mixture was concentrated in vacuo and purified using high-pressure liquid chromatography to yield 1-hydroxy-2-naphthoyl-L-arginyl-L-proline amide (41 mg, electrospray mass spectrum: $M^{+1}$=441), isolated as its trifluoroacetate salt.

B. Preparation of Compound 1 of Table III

By following the procedure of Part A above and substituting 2-benzyloxy-1-naphthoic acid for 1-benzyloxy-2-naphthoic acid and sarcosine amide for L-proline amide, there was obtained Compound 1 of Table III.

C. Preparation of Other Compounds of Formula I

By following the procedures of Part B above and substituting for sarcosine amide the following compounds:

L-proline-N,N-dimethylamide;

L-proline methyl ester; and trans-4-hydroxy-L-proline methyl ester;

there were obtained the following compounds:

Compound 5 of Tables I and II;

Compound 8 of Tables I and II; and

Compound 4 of Tables III.

V. Physical Data

TABLE I

| Compound | Mass Calculated | Mass Found ($M^{+1}$)[1] | LC Gradient[2] | LC Retention Time (min) |
|---|---|---|---|---|
| 1 | 414.24 | 415.1 | D | 5.8 |
| 2 | 404.26 | 405.5 | B | 11.5 |
| 3 | 440.26 | 441.1 | A | 10.3 |
| 4 | 471.26 | 472.2 | D | 6.2 |
| 5 | 468.29 | 469.1 | D | 6.8 |
| 6[3] | 551.34 | 552.3 | D | 7.5 |
| 7 | 551.34 | 552.1 | D | 7.3 |
| 8 | 455.26 | 456.0 | D | 7.0 |
| 9 | 442.26 | 443.0 | D | 5.5 |
| 10 | — | — | — | — |
| 11 | 456.26 | 456.7 | C | 24.4 |
| 12 | 440.26 | 441.2 | C | 25.4 |
| 13 | 587.34 | 588.0 | C | 26.9 |
| 14 | 440.26 | 440.5 | A | 9.0 |
| 15 | 440.26 | 440.2[4] | B | 8.4 |
| 16 | 391.5 | 391.8[4] | D | 5.6 |
| 17 | 456.49 | 456.7[4] | B | 9.0 |
| 18 | 393.22 | 391.8[4] | B | 5.5 |
| 19 | 390.4 | 391.1 | A | 4.7 |
| 20 | 406.4 | 407.2 | C | 20.7 |
| 21 | 466.5 | 467.2 | E | 3.5 |

[1]All masses were determined using a Finnigan electrospray mass spectrometer unless otherwise noted.

[2]A binary gradient system consisting of acetonitrile and water was used in all cases. All eluents contain 0.1% trifluoroacetic acid. A: 20–45% acetonitrile over 13 minutes. B: 10–35% acetonitrile over 13 minutes. C: 5–95% acetonitrile over 45 minutes. D: 2–95% acetonitrile over 10 minutes. E: 25–45% acetonitrile over 13 minutes.

[3]The material tested was a mixture of diastereomers.

[4]Masses determined using a Biolon mass spectrometer. Values represent $M^+$.

VI. In Vitro Tryptase Inhibition Assay

Compounds (approx. 1 mg) to be assayed against tryptase were reconstituted in dimethylsulfoxide (DMSO) and diluted 1:10 into buffer containing 50 millimolar (mM) Tris-HCl at pH 8.2, and containing 100 mM NaCl, 0.05% Tween-20. Seven additional 3-fold dilutions were made from the initial dilution into the same buffer supplemented with 10% DMSO. Aliquots (50 μl) from each of the eight dilutions in the series were transferred to individual wells in a 96-well U-bottom microtiter plate. Tryptase (25 μl; 0.5 nM final concentration) was added to each well and the samples were mixed and incubated for 1 hr at room temperature under either ambient light (i.e., the light available in the room during the experiment) or under controlled "light" or "dark" conditions. "Light conditions" refers herein to a light intensity of 400–450 footcandles from a fluorescent bulb. "Dark" refers herein to sample containers wrapped in aluminum foil. The enzyme reaction was then initiated with the addition of the synthetic tripeptide substrate, tosyl-GlyProLys-p-nitroanilide (25 μl; 0.5 mM final concentration). The microtiter plates were immediately transferred to a UV/MAX Kinetic Microplate Reader (Molecular Devices) and hydrolysis of the chromogenic substrate was followed spectrophotometrically at 405 nM for 5 minutes. The enzyme assays routinely yielded linear progress curves under these conditions. Initial velocity measurements, calculated from progress curves by a kinetic analysis program called "BatchKi" (available commercially from Biokin Ltd., of Madison Wis.), were used to determine apparent inhibition constants for each inhibitor. This program is designed to perform regressions and curve-fitting of non-linear data.

Table II lists the inhibition constants ($K_i'$, micromolar (μM)) which were determined for several of the compounds of the present invention, wherein $R^1$ is hydrogen; $R^2$ is hydrogen; $R^3$ is $-(CH_2)_3-NH-(C{=}NH)-NH_2$; $R^4$ and $R^5$, together with the nitrogen and carbon to which they are attached form a five-membered heterocycle; and $R^6$ is hydrogen. According to the present invention, a compound was termed "active" or effective as a tryptase inhibitor when its $K_i'$ was less than 1000 μM. Unlike $K_i$, $K_i'$ may not be a true dissociation constant of the enzyme-inhibitor complex; $K_i'$ is equal to $K_i$ for a noncompetitive inhibitor and is directly proportional to $K_i$ for competitive and uncompetitive inhibitors.

Exposure of solutions of the test compounds in the assay medium to light may decrease the $K_i'$. Generally, the assay conditions are light sensitive and variations in ambient light intensity may affect assay reproducibility. As a result of this potential source of error, some assays were run under dark conditions. The $K_i$'s reported in Tables II and III without parentheses were determined under conditions of ambient light. $K_i$'s reported with parentheses were determined under "dark" conditions as defined above. $K_i$'s reported with an asterisk (*) were measured under "light" conditions as defined above (i.e., at a light intensity of 400–450 footcandles).

TABLE II

| Compound | $K_i'$ | $R^7$ | Ar |
|---|---|---|---|
| 2 | >500 | $-NH_2$ | 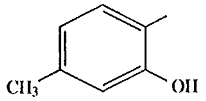 |
| 3 | 0.3* (82) | $-NH_2$ | 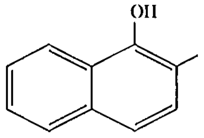 |
| 5 | 15 | $-N(CH_3)_2$ | 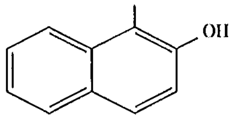 |
| 6 | 82 | 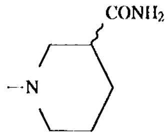 | 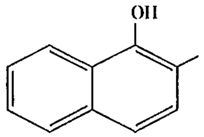 |
| 7 | 664 | 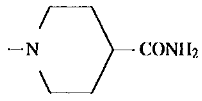 | 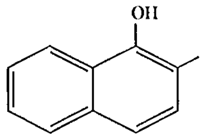 |
| 8 | 208 | $-OCH_3$ | 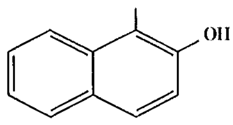 |
| 9 | 23* (56) | $-NH_2$ | 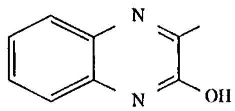 |

TABLE II-continued
| Compound | $K_i'$ | $R^7$ | Ar |
|---|---|---|---|
| 13 | 0.6* (110) | 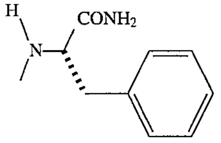 | 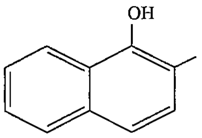 |
| 14 | 752* (707) | $-NH_2$ | 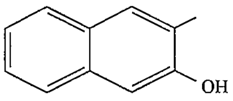 |
| 15 | 0.84 | $-NH_2$ | 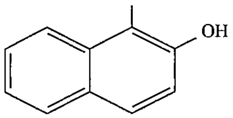 |
| 16 | 8* (63) | $-NH_2$ | 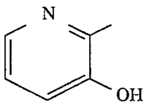 |
| 17 | 900 | $-NH_2$ | 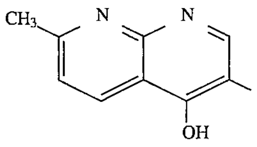 |
| 18 | 452 | $-NH_2$ | 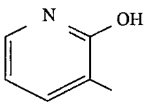 |
| 19 | 8* (2450) | $-NH_2$ | 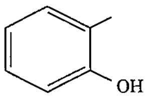 |
| 20 | 20 | $-NH_2$ | 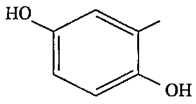 |
| 21 | 18* (149) | $-NH_2$ | 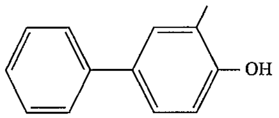 |
Table III lists the inhibition constants ($K_i'$, micromolar (μM)) which were determined for several of the compounds of the present invention. According to the present invention, a compound was termed "active" or effective as a tryptase inhibitor when its $K_i'$ was less than 1000 μM.

TABLE III
| Compound | $K_i'$ | Structure |
| --- | --- | --- |
| 1 | 3* (637) | 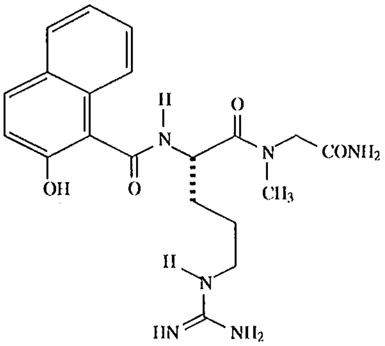 |
| 4 | 749 | 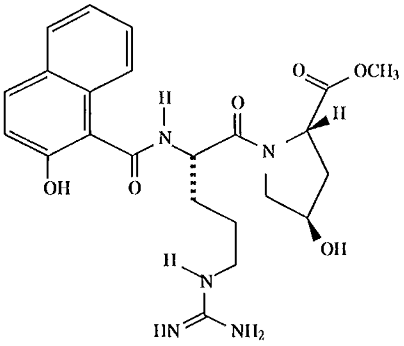 |
| 10 | 2.5* (18) | 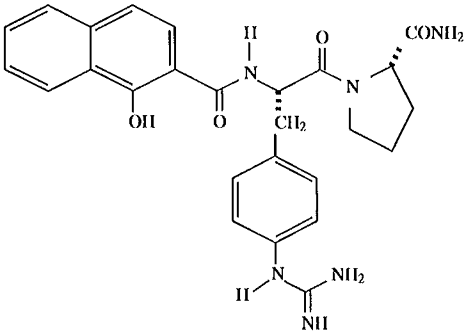 |
| 11 | 0.3* (40) | 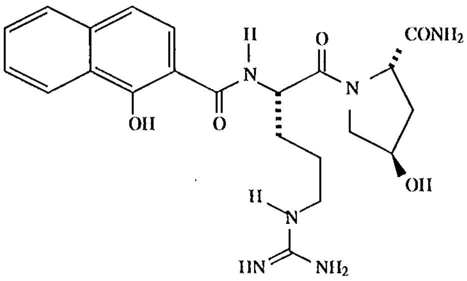 |

TABLE III-continued

| Compound | $K_i'$ | Structure |
|---|---|---|
| 12 | 2.5* (818) | 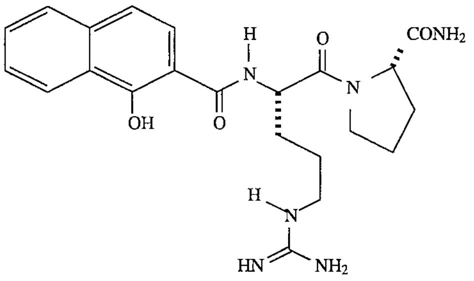 |

VII. Additional Characterization of Tryptase Inhibition by Compound 3 of Tables I and II A. pH Dependency Compound 3 was assayed against tryptase at four different pH's in the following buffer system: 120 mM NaCl, 2.7 mM KCl, 0.13 mM $NaH_2PO_4$, 0.896 mM $Na_2HPO_4$. The final buffer system used included 0.05% of Tween-20. Table IV shows $K_i'$ (μM) for Compound 3 at different pH's.

TABLE IV

| pH | 6.5 | 7.0 | 7.5 | 8.0 |
|---|---|---|---|---|
| $K_i'$ (μM) | 14 | 8.0 | 5.4 | 6.1 |

B. Optimized Assay at pH 7.5

The inventors have discovered that Compound 3 is less sensitive to light in the following buffer system: 120 mM NaCl, 2.7 mM KCl, 0.13 mM $NaH_2PO_4$, 0.896 mM $Na_2HPO_4$ and 0.05% Tween-20 at a pH of 7.5. Thus, the assay procedure described above was performed wherein the dilution of Compound 3 and the addition of tryptase was done under ambient light at room temperature (22°–26° C.). The assay plate was wrapped in aluminum foil for a 1-hr incubation before substrate addition, which was also done under ambient light. The steps of dilution and the addition of tryptase must be completed within 5 minutes. In addition, Compound 3 must be reconstituted in DMSO.

VIII. In Vivo Testing

The allergic sheep model of asthma was employed in these studies. These methods have been published previously (see Abraham et al. (1983) *Am. Rev. Respir. Dis.* 128:839–844; Allegra et al. (1983) *J. Appl. Physiol.* 55:726–730; Russi et al. (1985) *J. Appl. Physiol.* 59:1416–1422; Soler et al. ((1989) *J. Appl. Physiol.* 67:406–413. Each sheep served as its own control. Body weights for these animals ranged from 20–50 kilograms.

In these studies, 9 mg of Compound 3 of Tables I and II was dissolved in 3 mL buffered saline and the total solution delivered as an aerosol 0.5 hours before, 4 hours after, and 24 hours after antigen challenge (total dose=27; n=6). Compound 3 exhibited a tendency to reduce the early response, and attenuated the late response as shown in FIG. 1. In the control (vehicle only) trial, antigen challenge caused peak early and late increases above baseline in specific lung resistance (SRL) of 374±104% and 212±21% (mean±SE). In contrast, when the sheep were treated with Compound 3 of Tables I and II, the early and late increases in SRL were 280±39% and 72±9% ($p < 0.05$ vs. control, Wilcoxon signed rank test). The peak early response was taken as the average of the maximum values occurring immediately post-challenge. Peak late responses were calculated by averaging the maximum response values obtained for each animal within the 6–8 hour time period. This approach is conservative and eliminates the possible reduction in the late response due simply to averaging.

Figure 2:
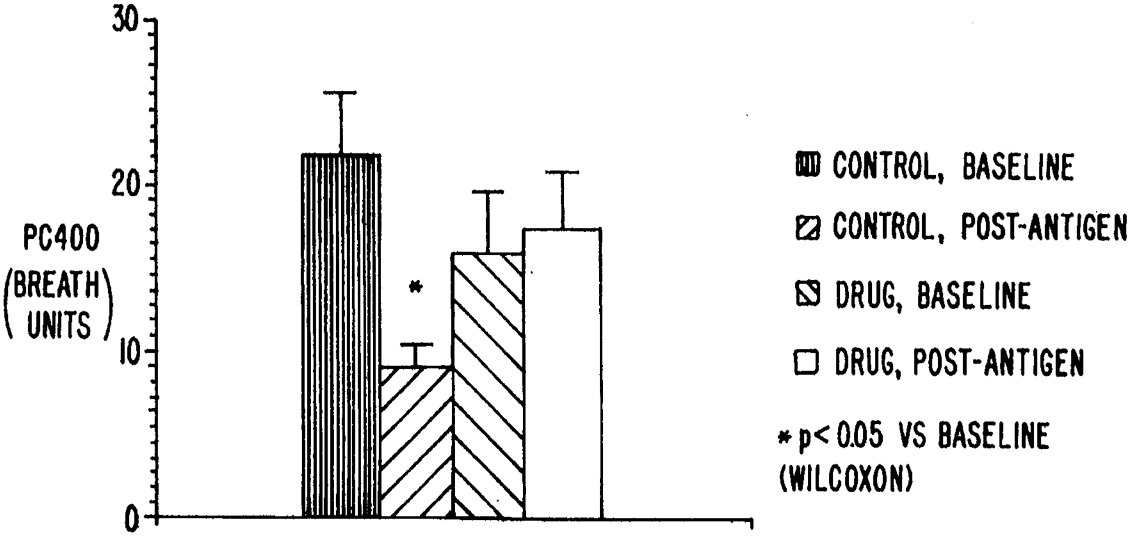
FIG. 2 is a graph showing production of hyperresponsiveness of sheep to carbachol-induced bronchoconstriction at 24 hours post-allergen challenge when Compound 3 of Tables I and II was administered before carbachol. The dark, solid bar corresponds to the control, baseline. The lighter, solid bar corresponds to the drug, baseline. The hatched bar corresponds to control, post-antigen. The white bar corresponds to the drug, post-antigen.

Twenty-four hours after antigen challenge in both the control and drug trial, the sheep developed airway hyperresponsiveness. (Airway hyperresponsiveness is expressed as PC400, i.e., the concentration of carbachol that causes a 400% increase in SRL. Thus a decrease in the PC400 indicates that the airways have become hyperresponsive.) Compound 3 of Tables I and II blocked the 24 hour hyperresponsiveness. See FIG. 2. Baseline PC400 was 22.0±3.7 breath units in the control trial, falling to 9.1±1.3 breath units after antigen challenge ($p<0.05$ vs. baseline). In contrast, in the drug trial, PC400 was unchanged relative to baseline (16.0±3.8 breath units vs. 17.6±3.5 breath units after antigen challenge). Thus treatment with Compound 3 of Tables I and II resulted in a statistically significant improvement in airway function in allergen challenged sheep.

The disclosures in this application of all articles and references, including patents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A compound having the formula:

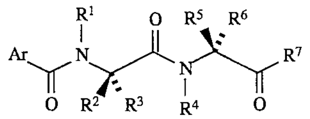

or a pharmaceutically acceptable salt thereof, wherein:

Ar is hydroxyl substituted aryl or hydroxyl substituted heteroaryl, wherein the hydroxyl is positioned ortho to the amide side chain and wherein if Ar is hydroxyl substituted aryl, the aromatic ring bearing the amide side chain is not substituted with halogen and does not bear a lower alkyl group on the position ortho to the hydroxyl;

$R^1$ is hydrogen, lower alkyl, arylalkyl, or heteroarylalkyl;

$R^2$ is hydrogen or lower alkyl;

$R^3$ is selected from the group consisting of:

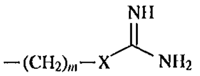

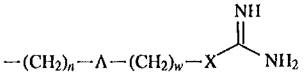

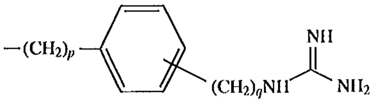

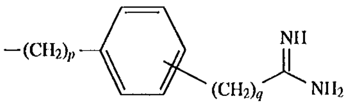

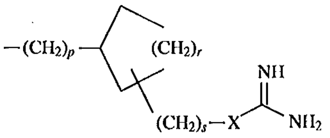

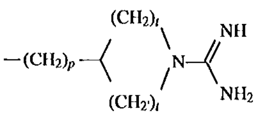

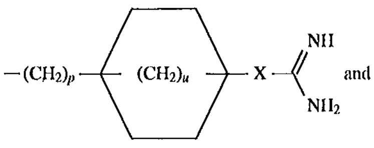 and $-(CH_2)_v-NH_2$ wherein m is an integer from 3–6, n is an integer from 0–3, p is an integer from 0–2, q is an integer from 0–2; r is an integer from 0–5; s is an integer from 0–2; t is an integer from 1–3; u is 1 or 2; v is an integer from 3–6; and w is an integer from 0–3; A is —CH═CH— or —C≡C—; and X is —NH— or —$CH_2$—;

$R^4$ is lower alkyl, substituted arylalkyl, or substituted heteroarylalkyl, $R^5$ and $R^6$ are independently selected from the group consisting of hydrogen, lower alkyl, substituted arylalkyl, and substituted heteroarylalkyl; or $R^4$ and $R^5$ together with the nitrogen and carbon to which they are attached form a substituted 4-membered, 5-membered, or 6-membered heterocycle and $R^6$ is hydrogen; or $R^4$ and $R^6$ together with the nitrogen and carbon to which they are attached form a substituted 4-membered, 5-membered, or 6-membered heterocycle and $R^5$ is hydrogen; and $R^7$ is —$OR^8$ or —$NR^8R^9$, wherein $R^8$ and $R^9$ are independently selected from the group consisting of hydrogen, lower alkyl, aryl, arylalkyl, or heteroarylalkyl or $R^8$ and $R^9$ together with the nitrogen to which they are attached, form a substituted 5-membered or 6-membered heterocycle.

2. The compound of claim 1 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

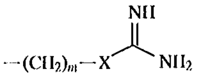

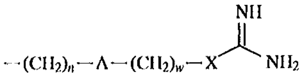

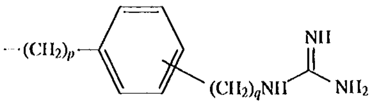

and

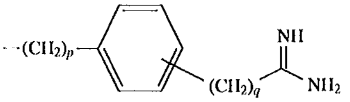

wherein m is an integer from 3–6, n is an integer from 0–3, p is an integer from 0–2, q is an integer from 0–2; and w is an integer from 0–3; A is —CH═CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen; and $R^7$ is —OH, —$OCH_3$, —$NH_2$, -3'aminocarboxy-1'-piperidyl, or —$N(CH_3)_2$.

3. The compound of claim 2 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

4. The compound of claim 2 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

5. An aerosol composition for the treatment of immunomediated inflammatory disorders comprising a compound of claim 1 in an aerosolized pharmaceutically acceptable carrier solution or dry powder.

6. The composition of claim 5 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

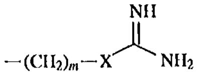

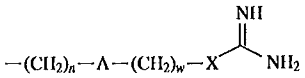

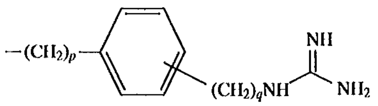

and

-continued

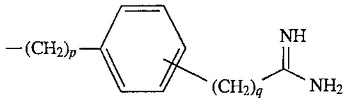

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

7. The composition of claim 6 wherein Ar is 1 -hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

8. The composition of claim 6 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

9. The composition of claim 5 wherein said inflammatory disorder of the respiratory tract is asthma.

10. The composition of claim 5 wherein said inflammatory disorder of the respiratory tract is allergic rhinitis.

11. The composition of claim 5 wherein said compound of claim 1 is present in said carrier solution in a concentration of from 0.1 to 30 mg/mL.

12. The composition of claim 5 further comprising a β-adrenergic agonist compound.

13. The composition of claim 12 wherein said β-adrenergic agonist compound is selected from the group consisting of albuterol, terbutaline, formoterol, fenoterol, and prenaline.

14. The composition of claim 5 further comprising an antiinflammatory corticosteroid.

15. The composition of claim 14 wherein said antiinflammatory corticosteroid is selected from the group consisting of beclomethasome, triamcinolone, flurisolide, and dexamethasone.

16. The composition of claim 5 further comprising ipratropium bromide.

17. A pharmaceutical composition comprising a compound of claim 1 in combination with a pharmaceutically acceptable carrier.

18. The composition of claim 17 wherein the pharmaceutically acceptable carrier comprises a non-toxic, pharmaceutically acceptable topical carrier.

19. The composition of claim 17 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

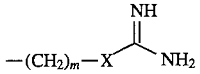

-continued

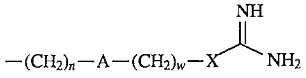

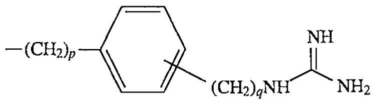

and

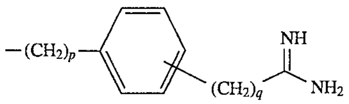

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

20. The composition of claim 19 wherein Ar is 1 -hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

21. The composition of claim 19 wherein Ar is 2 -hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

22. An aerosol device comprising:

a compound of claim 1 in a pharmaceutically acceptable carrier solution or dry powder, and means for converting said solution or dry powder into an aerosol form suitable for inhalation.

23. The device of claim 22 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

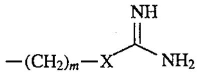

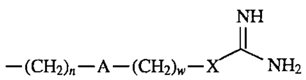

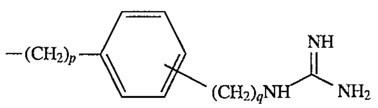

and

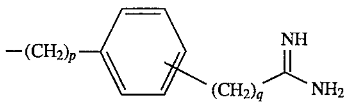

wherein m is an integer from 3–6, n is an integer from 0–3, p is an integer from 0–2, q is an integer from 0–2;

and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

24. The device of claim 23 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

25. The device of claim 23 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

26. The device of claim 22 wherein said compound is present in said carrier solution in a concentration of from 0.1 to 30 mg/mL.

27. The device of claim 22 further comprising a β-adrenergic agonist compound.

28. The device of claim 27 wherein said β-adrenergic agonist compound is selected from the group consisting of albuterol, terbutaline, formoterol, fenoterol, and prenaline.

29. The device of claim 22 further comprising an antiinflammatory corticosteroid.

30. The device of claim 29 wherein said antiinflammatory corticosteroid is selected from the group consisting of beclomethasone, triamcinolone, flurisolide, and dexamethasone.

31. The device of claim 22 further comprising ipratropium bromide.

32. A device for the treatment of allergic rhinitis comprising:

a compound of claim 1 in a pharmaceutically acceptable carrier solution, and means for converting said solution into an aerosol form suitable for intranasal administration.

33. The device of claim 32 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

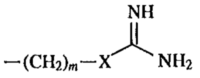

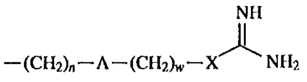

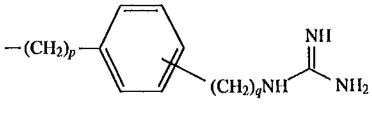

and

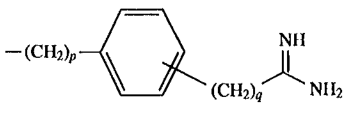

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

34. The device of claim 33 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

35. The device of claim 33 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

36. A method for treating an immunomediated inflammatory disorder of the respiratory tract, said method comprising administering to a mammal an inhalant composition comprising a compound of claim 1 in an aerosolized pharmaceutically acceptable carrier solution or dry powder.

37. The method of claim 36 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

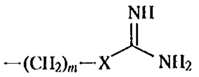

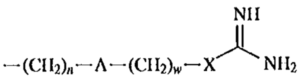

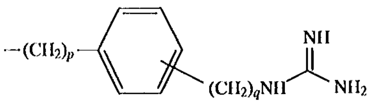

and

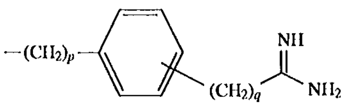

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

38. The method of claim 37 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

39. The method of claim 37 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

40. The method of claim 36 wherein said compound is present in said carrier solution in a concentration of from 0.1 to 30 mg/mL.

41. The method of claim 36 further comprising a β-adrenergic agonist compound.

42. The method of claim 41 wherein said β-adrenergic agonist compound is selected from the group consisting of albuterol, terbutaline, formoterol, fenoterol, and prenaline.

43. The method of claim 36 further comprising an anti-inflammatory corticosteroid.

44. The method of claim 43 wherein said antiinflammatory corticosteroid is selected from the group consisting of beclomethasome, triamcinolone, flurisolide, and dexamethasone.

45. The method of claim 36 further comprising ipratropium bromide.

46. A method for treating immunomediated inflammatory skin conditions, said method comprising administering topically to a mammal a composition comprising a therapeutically effective amount of a compound of claim 1 in a non-toxic, pharmaceutically acceptable topical carrier.

47. The method of claim 46 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

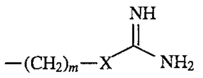

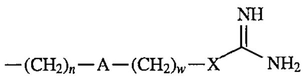

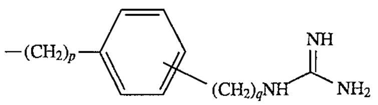

and

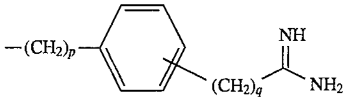

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

48. The method of claim 47 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

49. The method of claim 47 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

50. A method for prophylactically treating an immunomediated inflammatory disorder of the respiratory tract, said method comprising administering to a mammal an inhalant composition comprising a prophylactically effective amount of a compound of claim 1 in an aerosolized pharmaceutically acceptable carrier solution or dry powder.

51. The method of claim 50 wherein:

Ar is 1-hydroxy-2-naphthyl, 2-hydroxyl-1-naphthyl, 3-hydroxy-2-pyridyl, or 2-hydroxy-3-quinoxalyl;

$R^1$ is hydrogen;

$R^2$ is hydrogen;

$R^3$ is selected from the group consisting of:

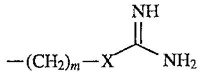

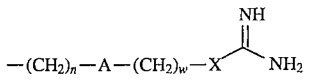

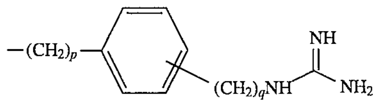

and

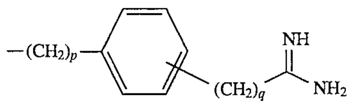

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl and $R^5$ and $R^6$ is hydrogen; or $R^4$ and $R^5$ together with the nitrogen and carbon to which they are attached form a substituted 4-membered, 5-membered, or 6-membered heterocycle and $R^6$ is hydrogen;

and $R^7$ is —OH, —$OCH_3$, —$NH_2$, -3'aminocarboxy-1'-piperidyl, or —$N(CH_3)_2$.

52. The method of claim 51 wherein Ar is 1-hydroxy-2-naphthyl, $R^1$ is hydrogen, $R^2$ is hydrogen $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

53. The method of claim 51 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted 5-membered heterocycle, $R^6$ is hydrogen, and $R^7$ is —$NH_2$.

54. The method of claim 50 wherein said compound is present in said carrier solution in a concentration of from 0.1 to 30 mg/mL.

55. The method of claim 50 further comprising a β-adrenergic agonist compound.

56. The method of claim 55 wherein said β-adrenergic agonist compound is selected from the group consisting of albuterol, terbutaline, formoterol, fenoterol, and prenaline.

57. The method of claim 50 further comprising an anti-inflammatory corticosteroid.

58. The method of claim 57 wherein said antiinflammatory corticosteroid is selected from the group consisting of beclomethasome, triamcinolone, flurisolide, and dexamethasone.

59. The method of claim 50 further comprising ipratropium bromide.

60. A compound having the formula:

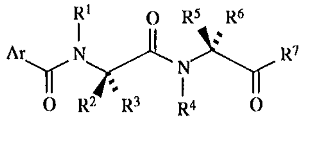

or a pharmaceutically acceptable salt thereof, wherein:

Ar is hydroxyl substituted aryl wherein the hydroxyl is positioned ortho to the amide side chain and wherein if Ar is hydroxyl substituted aryl, the aromatic ring bearing the amide side chain is not substituted with halogen and does not bear a lower alkyl or cycloalkyl group on the position ortho to the hydroxyl;

$R^1$ is hydrogen, lower alkyl, cycloalkyl or arylalkyl;

$R^2$ is hydrogen, lower alkyl or cycloalkyl;

$R^3$ is selected from the group consisting of:

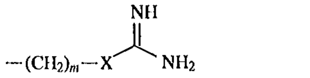

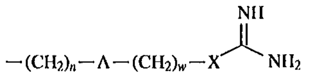

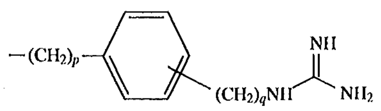

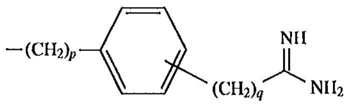

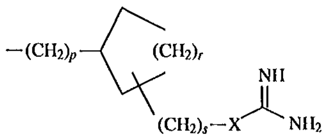

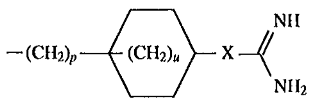

$-(CH_2)_v-NH_2$ wherein m is an integer from 3–6, n is an integer from 0–3, p is an integer from 0–2, q is an integer from 0–2; r is an integer from 0–5; s is an integer from 0–2; u is 1 or 2; v is an integer from 3–6; and w is an integer from 0–3; A is —CH=CH— or —C≡C—; and X is —NH— or —$CH_2$—;

$R^4$ is lower alkyl, cycloalkyl or substituted arylalkyl, $R^5$ and $R^6$ are independently selected from the group consisting of hydrogen, lower alkyl, cycloalkyl and substituted arylalkyl; or $R^4$ and $R^5$ together with the nitrogen and carbon to which they are attached form a substituted pyrrolidinyl ring and $R^6$ is hydrogen; or $R^4$ and $R^6$ together with the nitrogen and carbon to which they are attached form a substituted pyrrolidinyl ring and $R^5$ is hydrogen; and $R^7$ is —$OR^8$ or —$NR^8R^9$, wherein $R^8$ and $R^9$ are independently selected from the group consisting of hydrogen, lower alkyl, cycloalkyl, aryl and arylalkyl.

61. The compound of claim 60 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

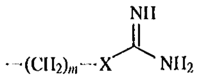

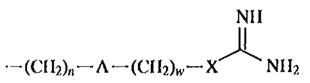

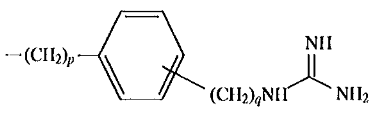

and

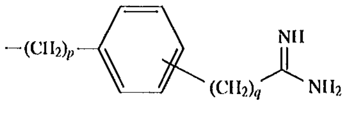

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is —OH, —$OCH_3$, —$NH_2$, or —$N(CH_3)_2$.

62. The compound of claim 61 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

63. The compound of claim 61 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

64. An aerosol composition for the treatment of immunomediated inflammatory disorders comprising a compound of claim 60 in an aerosolized pharmaceutically acceptable carrier solution or dry powder.

65. The composition of claim 64 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

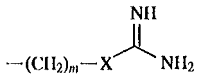

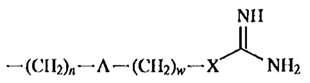

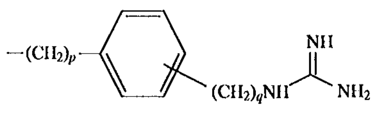

and

-continued

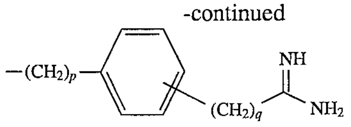

wherein m is an integer from 3–6, n is an integer from 0–3, p is an integer from 0–2, q is an integer from 0–2; and w is an integer from 0–3; A is —CH═CH— or —C≡C—; and X is —NH— or —$CH_2$—;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is —OH, —$OCH_3$, —$NH_2$, or —$N(CH_3)_2$.

66. The composition of claim 65 wherein Ar is 1 -hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

67. The composition of claim 65 wherein Ar is 2 -hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

68. The composition of claim 64 wherein said inflammatory disorder of the respiratory tract is asthma.

69. The composition of claim 64 wherein said inflammatory disorder of the respiratory tract is allergic rhinitis.

70. The composition of claim 64 wherein said compound of claim 60 is present in said carrier solution in a concentration of from 0.1 to 30 mg/mL.

71. The composition of claim 64 further comprising a β-adrenergic agonist compound.

72. The composition of claim 71 wherein said β-adrenergic agonist compound is selected from the group consisting of albuterol, terbutaline, formoterol, fenoterol, and prenaline.

73. The composition of claim 64 further comprising an antiinflammatory corticosteroid.

74. The composition of claim 73 wherein said antiinflammatory corticosteroid is selected from the group consisting of beclomethasone, triamcinolone, flurisolide, and dexamethasone.

75. The composition of claim 64 further comprising ipratropium bromide.

76. A pharmaceutical composition comprising a compound of claim 60 in combination with a pharmaceutically acceptable carrier.

77. The composition of claim 76 wherein the pharmaceutically acceptable carrier comprises a non-toxic, pharmaceutically acceptable topical carrier.

78. The composition of claim 76 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

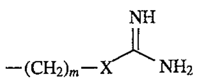

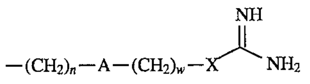

-continued

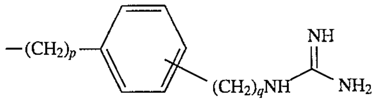

and

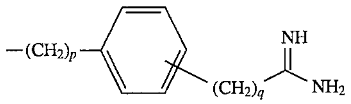

wherein m is an integer from 3–6, n is an integer from 0–3, p is an integer from 0–2, q is an integer from 0–2; and w is an integer from 0–3; A is —CH═CH— or —C≡C—; and X is —NH— or —$CH_2$—;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is —OH, —$OCH_3$, —$NH_2$, or —$N(CH_3)_2$.

79. The composition of claim 78 wherein Ar is 1 -hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

80. The composition of claim 78 wherein Ar is 2 -hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

81. An aerosol device comprising:

a compound of claim 60 in a pharmaceutically acceptable carrier solution or dry powder, and means for converting said solution or dry powder into an aerosol form suitable for inhalation.

82. The device of claim 81 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

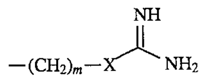

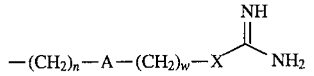

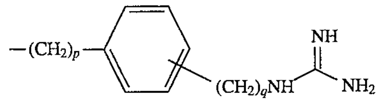

and

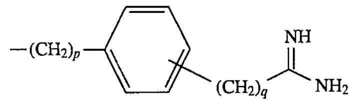

wherein m is an integer from 3–6, n is an integer from 0–3, p is an integer from 0–2, q is an integer from 0–2; and w is an integer from 0–3; A is —CH═CH— or —C≡C—; and X is —NH— or —$CH_2$—;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is $-OH$, $-OCH_3$, $-NH_2$, or $-N(CH_3)_2$.

83. The device of claim 82 wherein Ar is 1-hydroxy-2-naphthyl, $R^1$ is hydrogen, $R^2$ is hydrogen, $R^3$ is $-(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is $-NH_2$.

84. The device of claim 82 wherein Ar is 2-hydroxy-1-naphthyl, $R^1$ is hydrogen, $R^2$ is hydrogen, $R^3$ is $-(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is $-NH_2$.

85. The device of claim 81 wherein said compound is present in said carrier solution in a concentration of from 0.1 to 30 mg/mL.

86. The device of claim 81 further comprising a β-adrenergic agonist compound.

87. The device of claim 86 wherein said β-adrenergic agonist compound is selected from the group consisting of albuterol, terbutaline, formoterol, fenoterol, and prenaline.

88. The device of claim 81 further comprising an antiinflammatory corticosteroid.

89. The device of claim 88 wherein said antiinflammatory corticosteroid is selected from the group consisting of beclomethasone, triamcinolone, flurisolide, and dexamethasone.

90. The device of claim 81 further comprising ipratropium bromide.

91. A device for the treatment of allergic rhinitis comprising:

a compound of claim 60 in a pharmaceutically acceptable carrier solution, and means for converting said solution into an aerosol form suitable for intranasal administration.

92. The device of claim 91 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

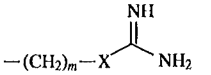

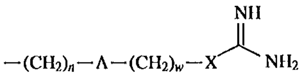

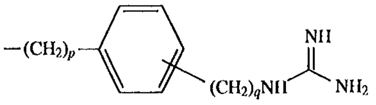

and

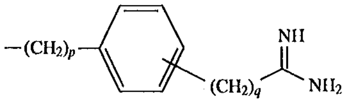

wherein m is an integer from 3–6, n is an integer from 0–3, p is an integer from 0–2, q is an integer from 0–2; and w is an integer from 0–3; A is $-CH=CH-$ or $-C\equiv C-$; and X is $-NH-$ or $-CH_2-$;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is $-OH$, $-OCH_3$, $-NH_2$, or $-N(CH_3)_2$.

93. The device of claim 92 wherein Ar is 1-hydroxy-2-naphthyl, $R^1$ is hydrogen, $R^2$ is hydrogen, $R^3$ is $-(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is $-NH_2$.

94. The device of claim 92 wherein Ar is 2-hydroxy-1-naphthyl, $R^1$ is hydrogen, $R^2$ is hydrogen, $R^3$ is $-(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is $-NH_2$.

95. A method for treating an immunomediated inflammatory disorder of the respiratory tract, said method comprising administering to a mammal an inhalant composition comprising a compound of claim 60 in an aerosolized pharmaceutically acceptable carrier solution or dry powder.

96. The method of claim 95 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

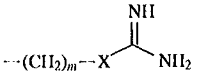

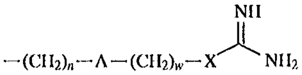

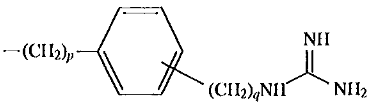

and

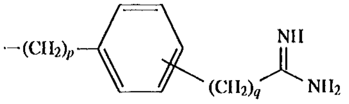

wherein m is an integer from 3–6, n is an integer from 0–3, p is an integer from 0–2, q is an integer from 0–2; and w is an integer from 0–3; A is $-CH=CH-$ or $-C\equiv C-$; and X is $-NH-$ or $-CH_2-$;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is $-OH$, $-OCH_3$, $-NH_2$, or $-N(CH_3)_2$.

97. The method of claim 96 wherein Ar is 1-hydroxy-2-naphthyl, $R^1$ is hydrogen, $R^2$ is hydrogen, $R^3$ is $-(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is $-NH_2$.

98. The method of claim 96 wherein Ar is 2-hydroxy-1-naphthyl, $R^1$ is hydrogen, $R^2$ is hydrogen, $R^3$ is $-(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is $-NH_2$.

99. The method of claim 95 wherein said compound is present in said carrier solution in a concentration of from 0.1 to 30 mg/mL.

100. The method of claim 95 further comprising a β-adrenergic agonist compound.

101. The method of claim 100 wherein said β-adrenergic agonist compound is selected from the group consisting of albuterol, terbutaline, formoterol, fenoterol, and prenaline.

102. The method of claim 95 further comprising an antiinflammatory corticosteroid.

103. The method of claim 102 wherein said antiinflammatory corticosteroid is selected from the group consisting of beclomethasone, triamcinolone, flurisolide, and dexamethasone.

104. The method of claim 95 further comprising ipratropium bromide.

105. A method for treating immunomediated inflammatory skin conditions, said method comprising administering topically to a mammal a composition comprising a therapeutically effective amount of a compound of claim 60 in a non-toxic, pharmaceutically acceptable topical carrier.

106. The method of claim 105 wherein:

Ar is 1-hydroxy-2-naphthyl or 2-hydroxyl-1-naphthyl;

$R^1$ is hydrogen;

$R^2$ is hydrogen;

$R^3$ is selected from the group consisting of:

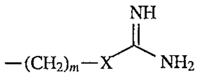

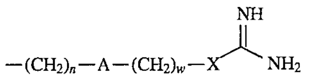

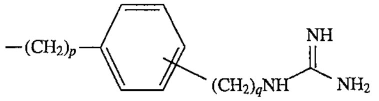

and

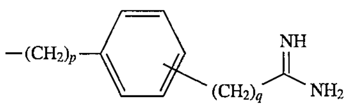

wherein m is an integer from 3–6, n is an integer from 0–3, p is an integer from 0–2, q is an integer from 0–2; and w is an integer from 0–3; A is —CH=CH— or —C≡C—; and X is —NH— or —$CH_2$—;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is —OH, —$OCH_3$, —$NH_2$, or —$N(CH_3)_2$.

107. The method of claim 106 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

108. The method of claim 106 wherein Ar is 2-hydroxy-1-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

109. A method for prophylactically treating an immunomediated inflammatory disorder of the respiratory tract, said method comprising administering to a mammal an inhalant composition comprising a prophylactically effective amount of a compound of claim 60 in an aerosolized pharmaceutically acceptable carrier solution or dry powder.

110. The method of claim 109 where:

Ar is 1-hydroxy-2-naphthyl or 2-hydroxyl-1-naphthyl;

$R^1$ is hydrogen;

$R^2$ is hydrogen;

$R^3$ is selected from the group consisting of:

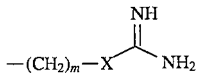

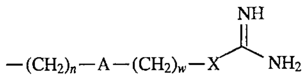

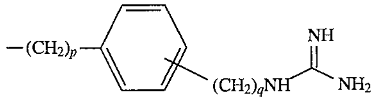

and

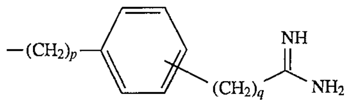

wherein m is an integer from 3–6, n is an integer from 0–3, p is an integer from 0–2, 1 is an integer from 0–2; and w is an integer from 0–3; A is —CH=CH— or —CH≡C—; and X is —NH— or —$CH_2$—;

$R^4$ is lower alkyl or cycloalkyl, and $R^5$ and $R^6$ are hydrogen; or $R^4$ and $R^5$ together with the nitrogen and carbon to which they are attached form a substituted pyrrolidinyl ring and $R^6$ is hydrogen;

and $R^7$ is —OH, —$OCH_3$, —$NH_2$, or —$N(CH_3)_2$.

111. The method of claim 110 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

112. The method of claim 110 wherein Ar is 1-hydroxy-2-naphthyl, $R^1$ is hydrogen, $R^2$ is hydrogen, $R^3$ is —$(CH_2)_3NH(CNH)NH_2$, $R^4$ and $R^5$ along with the nitrogen and carbon to which they are attached form a substituted pyrrolidinyl ring, $R^6$ is hydrogen, and $R^7$ is —$NH_2$.

113. The method of claim 109 wherein said compound is present in said carrier solution in a concentration of from 0.1 to 30 mg/mL.

114. The method of claim 109 further comprising a β-adrenergic agonist compound.

115. The method of claim 114 wherein said β-adrenergic agonist compound is selected from the group consisting of albuterol, terbutaline, formoterol, fenoterol, and prenaline.

116. The method of claim 109 further comprising an antiinflammatory corticosteroid.

117. The method of claim 116 wherein said antiinflammatory corticosteroid is selected from the group consisting of beclomethasone, triamcinolone, flurisolide, and dexamethasone.

118. The method of claim 109 further comprising ipratropium bromide.

* * * * *